(12) United States Patent
Xu et al.

(10) Patent No.: US 7,632,878 B2
(45) Date of Patent: Dec. 15, 2009

(54) DENTAL RELEASING MATERIALS

(75) Inventors: Huakun Xu, Frederick, MD (US); Limin Sun, Germantown, MD (US); Shozo Takagi, Gaithersburg, MD (US); Laurence C. Chow, Potomac, MD (US)

(73) Assignee: American Dental Association Foundation, Chicago, IL (US)

( * ) Notice: Subject to any disclaimer, the term of this patent is extended or adjusted under 35 U.S.C. 154(b) by 0 days.

(21) Appl. No.: 12/288,183

(22) Filed: Oct. 17, 2008

(65) Prior Publication Data
US 2009/0093566 A1 Apr. 9, 2009

Related U.S. Application Data

(63) Continuation of application No. 11/439,850, filed on May 24, 2006, now abandoned, which is a continuation-in-part of application No. 11/138,182, filed on May 26, 2005, now abandoned.

(51) Int. Cl.
*A61K 6/083* (2006.01)
*C08K 3/32* (2006.01)
*C08K 3/34* (2006.01)
*A61C 5/00* (2006.01)

(52) U.S. Cl. ................ 523/116; 524/414; 524/493; 433/228.1

(58) Field of Classification Search ............. 523/116; 433/228.1; 524/414, 493
See application file for complete search history.

(56) References Cited

U.S. PATENT DOCUMENTS

| | | | |
|---|---|---|---|
| 4,612,053 | A | 9/1986 | Brown et al. |
| 4,813,876 | A | 3/1989 | Wang |
| 5,508,342 | A | 4/1996 | Antonucci et al. |
| 5,652,016 | A | 7/1997 | Imura et al. |
| 5,695,729 | A | 12/1997 | Chow et al. |
| 5,814,681 | A | 9/1998 | Hino et al. |
| 5,861,445 | A | 1/1999 | Xu et al. |
| 6,334,775 | B2 | 1/2002 | Xu et al. |
| 6,398,859 | B1 | 6/2002 | Dickens et al. |
| 6,693,143 | B2 * | 2/2004 | Pflug ............ 523/116 |
| 2002/0156152 | A1 | 10/2002 | Zhang et al. |
| 2003/0147956 | A1 | 8/2003 | Shefer et al. |
| 2003/0167093 | A1 | 9/2003 | Xu et al. |
| 2003/0181541 | A1 | 9/2003 | Wu et al. |
| 2004/0086446 | A1 | 5/2004 | Jia et al. |
| 2005/0020720 | A1 * | 1/2005 | Dickens et al. ......... 523/115 |
| 2005/0260269 | A1 * | 11/2005 | Engelbrecht et al. ...... 424/486 |

FOREIGN PATENT DOCUMENTS

JP 408157658 A 6/1996

OTHER PUBLICATIONS

Chow et al., Properties of Nanostructured Hydroxyapatite Prepared by a Spray Drying Technique, J. Res. Natl. Inst. Stand. Technol. 109, 543-551 (2004).
McLean, Cermet Cements, JADA, (Jan. 1990) pp. 43-47, vol. 120.
Pool Thong et al., A Comparison of the Mechanical Properties of Three Glass-Ionomer Cements, Dental Materials Journal (1994) pp. 220-227, vol. 13(2).
Bayne et al., Update on Dental Composite Restorations, JADA (Jun. 1994) pp. 687-701, vol. 125.
Skrtic et al., Quantitative Assessment of the Efficacy of Amorphous Calcium Phosphate/Methacrylate Composites in Remineralizing Caries-Like Lesions Artificially Produced in Bovine Enamel, J. Dent Res (Sep. 1996) pp. 1679-1686, vol. 75(9).
Skrtic et al., Improved Properties of Amorphous Calcium Phosphate Fillers in Remineralizing Resin Composites, Dental Material (Sep. 1996) pp. 295-301, vol. 12:295.
Ferracane et al., In Vitro Aging of Dental Composites in Water—Effect of Degree of Conversion, Filler Volume, and Filler/Matrix Coupling, Department of Biomaterials and Biomechanics, Oregon Health Sciences University (1998) pp. 465-472.
Xu et al., Ceramic Whisker Reinforcement of Dental Resin Composites, J. Dent. Res (Feb. 1999) pp. 706-712, vol. 78(2).
Donly et al., A Clinical Comparison of Resin Composite Inlay and Onlay Posterior Restorations and Cast-Gold Restorations at 7 Years, Quintessence International (1999) pp. 163-168, vol. 30(3).
Christensen, Porcelain-Fused-To-Metal vs. Nonmetal Crowns, JADA (Mar. 1999) pp. 409-412, vol. 130.
Xu, Whisker-Reinforced Heat-Cured Dental Resin Composites: Effects of Filler Level and Heat-Cure Temperature and Time, J. Dent Res (2000) pp. 1392-1397, vol. 79(6).
Skrtic et al., Physicochemical Evaluation of Bioactive Polymeric Composites Based on Hybrid Amorphous Calcium Phosphates (2000) pp. 381-391.
Summitt et al., Fundamentals of Operative Dentistry—A Contemporary Approach, Second Edition (2001) Chapter 8 pp. 178-235.
Dickens et al., Mechanical Properties and Biochemcial Activity of Remineralizing Resin-Based Ca-PO4 Cements, Dental Materials (2003) pp. 558-566, vol. 19.
Sarrett, Clinical Challenges and the Relevance of Materials Testing for Posterior Composite Restorations, Dental Materials (2005) pp. 9-20, vol. 21.
Sakaguchi, Review of the Current Status and Challenges for Dental Posterior Restorative Composites; Clincal, Chemistry, and Physical Behavior Considerations, Dental Materials (2005) pp. 3-6, vol. 21.
Sun et al., Preparation and Properties of Nano-sized Calcium Fluoride for Dental Applications, Dental Materials (Nov. 2006) pp. 1-20.

* cited by examiner

*Primary Examiner*—Tae H Yoon
(74) *Attorney, Agent, or Firm*—Banner & Witcoff, Ltd.

(57) ABSTRACT

Combining nanosized particles of a source of desired dental restorative, repair or therapeutic materials with strengthening agents in various generally nanosized form such as whiskers, fibers, particles and the like in a resin matrix provides a highly strain resistant composite which more effectively releases the therapeutic agents. The utilization of nano sized particles of the therapeutic agent in the combination enables observation of significantly improved therapeutic results.

5 Claims, 15 Drawing Sheets

MCPM Nano Composites, Direct-Filling, with HEMA

MCPM Nano Composites, Direct-Filling, with HEMA

MCPM Nano Composites, Direct-Filling, no HEMA

MCPM Nano Composites, Indirect Restorations, Heat-Cured

DCPA Nano Composites, Direct-Filling, with HEMA

Nano DCPA Composite with Different Strengtheners

Nano DCPA-TTCP dental composite

Nano CaF$_2$-DCPA composite

Calcium phosphate dental composite
Acid neutralization: effect of particle size

DENTAL RELEASING MATERIALS

CROSS REFERENCE TO RELATED APPLICATIONS

This is a continuation application of previously filed utility application Ser. No. 11/439,850 filed May 24, 2006 entitled "Dental Releasing Materials"(now abandoned) which is a continuation-in-part application of previously filed utility application Ser. No. 11/138,182, filed May 26, 2005, entitled "Dental Releasing Materials" (now abandoned) for which priority is claimed and which is incorporated herewith by reference.

BACKGROUND OF THE INVENTION

In a principal aspect the present invention relates to two major problems facing current dental composites; namely, secondary caries and bulk fracture. The invention is directed to new dental materials that overcome these problems by being extremely strong mechanically to resist fracture and by being able to simultaneously release agents to combat caries.

Specifically, an object of the invention is to (1) provide new dental materials having nano calcium phosphate and/or other fillers capable of substantial release of calcium, phosphate and/or fluoride to combat tooth decay; (2) tailor the nano releasing filler/strengthening filler ratio and the fast releasing filler/slow releasing filler ratio to control the release profile and provide superior resistance to chewing forces; and (3) provide novel compositions for dental restorations, stress-bearing applications, artificial crowns, anterior and posterior tooth fillings, adhesives, cavity liners, cements, bases, orthodontic devices, prostheses, and sealants.

The new materials are substantially stronger than currently available stress-bearing composites, yet the new composites include release agents useful to combat tooth caries, while the currently available stress-bearing composites do not.

That is, known current composites that do possess release capabilities for calcium and phosphate, etc. are too weak mechanically for large stress-bearing applications. The new composites are not only much stronger, but can also release more calcium and phosphate ions than known prior art composites.

Dental composites are composed of a mixture of fillers with a hardenable matrix, for example, an acrylic monomer (also termed resin or dental resin), that is polymerized or hardened to form a composite restoration. The two most major clinical problems of current dental composites have been: restoration fracture, and secondary caries. A recent review article shows that "clinical data indicate that the two main challenges are secondary caries and bulk fracture" (Sarrett, Clinical challenges and the relevance of materials testing for posterior composite restorations, Dent Mater, 21:9-20, 2005).

Two classes of dental materials have been developed to address these issues. The first class is termed stress-bearing materials, and the second class is termed releasing materials. Stress-bearing materials include dental composites that are developed with the purpose of being used in large stress-bearing restorations. Releasing materials release calcium, phosphate, fluoride and other agents to prevent tooth decay and to repair or remineralize tooth structures that have already decayed or lost tooth minerals.

Problem I. Restoration Fracture

Stress-bearing dental composites have been significantly enhanced (for example, see Ferracane et al., J Biomed Mater Res 42:465-472, 1998). However, dental composites "are not recommended for large posterior restorations because of the potential for excessive wear, microleakage or fracture" (Bayne et al., J Am Dent Assoc 125:687-701, 1994). For filled polymer composite crowns, fracture during service has been observed and the composites have lost favor as they continued to fail (Christensen, J Am Dent Assoc 130:409-411, 1999). Even for small inlay restorations, while the 7-year clinical failure rate of a composite for premolar inlays was relatively low, nearly half of the stress-bearing molar inlays had failed at 7 years (Donly et al., Quintessence Intl 30:163-169, 1999). Therefore, it is recognized that "some properties might be satisfactory for smaller restorations, but insufficient for larger restorations" (Sakaguchi, Dent Mater 21:3-6, 2005).

The strength of dental composites is generally considered to be adequately measured in a flexural test. Although the direct measurement of tensile strength may have validity, it is technically difficult to execute. The compressive strength is only indirectly related, in a complex manner, to a combination of tensile and shear failure modes. The measurement of diametral tensile strength requires that the material exhibits no plastic flow, which does not hold true for the majority of dental composites. Therefore, the flexural test has been utilized to characterize the mechanical properties of dental composites. Currently-available dental composites for stress-bearing restorations usually have flexural strength values ranging from 80 MPa (1 MPa=$10^6$ N/m$^2$; N=Newton, m=meter) to about 120 MPa (Xu et al., J Dent Res 78:706-712, 1999). Their fracture toughness (resistance to cracking) ranges from about 0.9 MPa·m$^{1/2}$ to 1.1 MPa·m$^{1/2}$ (Xu, J Dent Res 79:1392-1397, 2000). Further improvements are needed for composites to overcome brittle fracture and high failure rates in high stress-bearing restorations (Christensen, J Am Dent Assoc 130:409-411, 1999; Donly et al., Quintessence Intl 30:163-169, 1999), especially those that are large in restoration size and involve the replacement of tooth cusps.

Problem II. Secondary Caries

The terms "caries", "cavities" and "tooth decay" refer to the demineralization or dissolution of tooth mineral. The term "demineralization" refers to the loss of mineral in tooth structure, resulting in mineral-deficient lesions. The terms "remineralization", "mineralization" and similar terms mean the formation of solid inorganic structures similar to the mineral in natural teeth. "Secondary caries" refers to the recurrence of demineralization at a certain period of time after the primary caries is removed and the tooth cavity is restored.

Secondary caries is often cited as a major reason for the replacement of existing composite restorations (Sarrett, Dent Mater, 21:9-20, 2005). Glass ionomers, resin-modified glass ionomers and compomers are developed to release fluoride into adjacent tooth structure to combat caries. Glass ionomers refer to dental materials that are based on the acid-base reaction of an aqueous solution of a polycarboxylic acid with an ion leachable, fluoride-containing glass. However, the brittleness and inferior mechanical properties of glass ionomers (flexural strength of 10-20 MPa) have severely limited their use. Resin-modified glass ionomers use resins (for example, 2-hydroxyethyl methacrylate, or HEMA) with the polyacids. The name compomer is derived by combining the two words composite and ionomer, and is intended to suggest a combination of composite and glass-ionomer technology. They are modified in their resin phase by a carboxylic acid monomer, and in their filler phase by the inclusion of an acid-reactive, ion-leachable glass. Resin-modified glass ionomers and compomers are not recommended for use in large, stress-bearing restorations.

Other materials release calcium ($Ca^{2+}$) and phosphate ($PO_4$) ions to form hydroxyapatite (HA), $Ca_{10}(PO_4)_6(OH)_2$, which is the putative mineral in natural teeth (Skrtic et al., J Dent Res 75:1679-1686, 1996; Dickens et al., Dent Mater 19:558-566, 2003). These materials are highly promising for remineralizing the decayed teeth and help prevent the occurrence of caries. These novel composites possess diametral tensile strength of 10 MPa to 30 MPa, and flexural strength of 50 MPa to 70 MPa. While their calcium and phosphate release have excellent remineralization capability, these composites are not strong enough for use in large-stress restorations or fillings that replace tooth cusps.

U.S. Pat. No. 4,612,053 (Brown et al.) and U.S. Pat. No. 5,695,729 (Chow et al.) disclose self-setting calcium phosphate cements (CPC) consisting of tetracalcium phosphate (TTCP) and dicalcium phosphate anhydrous (DCPA) or dihydrate (DCPD). U.S. Pat. No. 5,652,016 (Imura et al.) discloses calcium phosphate cement compositions. CPCs are excellent bone repair materials because they can harden in situ in the bone cavity. Hydroxyapatite is relatively stable with minimal release of calcium and phosphate ions, hence CPC is not being used to remineralize decayed tooth structures. In addition, there is no mention of using CPC in large stress-bearing tooth restorations. This is because the flexural strength of about 10 MPa for CPC is not generally sufficient to survive the chewing forces.

U.S. Pat. No. 4,813,876 (Wang) discloses calcium hydroxide-containing polymerizable cavity liner. Because it does not have a phosphate component, it does not teach the remineralization capacity to form hydroxyapatite.

U.S. Pat. No. 5,508,342 (Antonucci et al.) discloses polymeric releasing compositions containing amorphous calcium phosphate (ACP). They release calcium and phosphate ions with concentrations of about 1.0 mmol/L ($=10^{-3}$ mole/liter) for calcium and 0.25-0.8 mmol/L for phosphate ions. These composites are highly promising for remineralizing decayed tooth structures and in preventing demineralization. However, there are three drawbacks. First, the ACP powders are weak mechanically, hence it is recognized that they do not act as reinforcing fillers (Skrtic et al., J Biomed Mater Res Appl Biomater 53:381-391, 2000). Second, the low filler level (inorganic/[inorganic+hardenable matrix]) of 40% mass fraction means that the composite consists of mostly resin. Low filler level results in high polymerization shrinkage, yielding undesirable internal stresses in the tooth cavity. Third, flexural strength of 50-70 MPa for the ACP composite is relatively low compared to 80-120 MPa for currently available stress-bearing composites. Even the latter exhibit bulk fracture in large stress-bearing restorations. Hence these releasing materials do not have the fracture toughness and wear resistance to resist chewing forces for large cavities or load-bearing restorations.

U.S. Pat. No. 5,814,681 (Hino et al.) discloses a composition containing calcium phosphate powder and polymerizable monomer. It is for bone repair. There is no mention of calcium and phosphate release nor remineralization of tooth structures.

U.S. Pat. No. 6,398,859 discloses resin-based pulp-capping and remineralizing cements. Examples of cements comprise the combination of a paste 1 and either a paste 2 or a powder, wherein paste 1 contains dicalcium phosphate and other components, and paste 2 or the powder contains tetracalcium phosphate. This material not only exhibits a high pH of around 10 during hardening to stimulate new dentin formation in pulp capping, but also releases calcium and phosphate ions to form hydroxyapatite and remineralize decayed tooth structures. Therefore, it has the excellent ability to act in the dual manner as a pulp capping cement while simultaneously promoting the repair of mineral-deficient tooth structure through the precipitation of tooth-like minerals. Its diametral tensile strength of 10-30 MPa is sufficient for pulp capping applications. These materials release concentrations of about 0.05-0.5 mmol/L of calcium and 0.3-1.0 mmol/L of phosphate ions (Dickens et al., Dental Materials 19:558-566, 2003). These materials are for pulp-capping and base/lining cement and other dental cements applications. They are not suggested for large stress-bearing restorations, wear-resistant restorations, or fillings that involve tooth cusps.

U.S. Pat. No. 5,861,445 (Xu et al.) and U.S. Pat. No. 6,334,775 (Xu et al.) disclose dental composites containing whiskers and fibers within a hardenable matrix. There is no mention of using nano-sized calcium phosphate fillers or the release of calcium and phosphate ions for the remineralization of decayed tooth structures. There is no teaching of a method of controlling the $Ca^{2+}$ and $PO_4$ release profile by tailoring the nano releasing filler/strengthening filler ratio or the fast releasing filler/slow releasing filler ratio.

U.S. Pat. application 20020156152 (Zhang et al.) and application 20030181541 (Wu et al.) disclose dental materials with nano-sized silica particles. Diametral tensile strength of 62-68 MPa is achieved. There is no mention of using calcium and phosphate fillers; there is no release of calcium and phosphate ions; and there is no teaching on remineralization of decayed teeth.

U.S. Pat. application 20030147956 (Shefer et al.) discloses controlled release for site specific delivery of biologically active ingredients for oral care. It is not related to tooth cavity fillings and restorations, nor is it related to polymers and resin composites.

U.S. Pat. application 20040086446 (Jia et al.) discloses dental resin materials with nano silica fillers. There is no mention of using nano-sized calcium phosphate fillers, and there is no teaching of remineralizing the decayed tooth structures.

Prior art, stress-bearing composites appear to have flexural strength of 80-120 MPa, but do not have calcium or phosphate ion release. They can survive in moderate-stress applications, but they exhibit bulk fracture in large stress-bearing restorations, especially those that involve tooth cusps. Releasing composites have strengths of 30-70 MPa. There is no description, of dental composites that have flexural strength of 140-170 MPa together with substantial release, which are described in this application which are not only 100%-500% higher than the releasing composites in the prior art, but also 40%-100% higher than the stress-bearing composites without release as reported by prior art.

In addition, in the prior art, the releasing materials release calcium and phosphate at concentrations of 0.1 to 1 mmol/L. There is no mention of dental composites that release calcium and phosphate ions with concentrations of 2 to 7 mmol/L and as high as 16 mmol/L. Such new dental composites are described in the present application.

SUMMARY OF THE INVENTION

Briefly, the present invention comprises new composites that contain nano-sized calcium phosphate fillers and/or fluoride releasing fillers for substantial calcium ($Ca^{2+}$) and phosphate ($PO_4$) release and/or $F^-$ release, together with reinforcement fillers to provide superior strength and fracture toughness. Current dental composites include either stress-bearing composites or releasing composites. Stress-bearing composites in the prior art have flexural strength of 80-120 MPa, but have no release. They can survive in moderate stress-bearing applications, but they experience bulk fracture in large stress-bearing restorations. Releasing composites in the prior art use the same releasing fillers as reinforcement which provide poor or no reinforcement, and hence they have strengths of 30-70 MPa.

The new composites of this invention have flexural strength of up to 140-170 MPa together with high levels of release. Composites in the prior art that release $Ca^{2+}$ and $PO_4$ can reach ion concentrations of about 0.05 mmol/L to 1 mmol/L. The releasing filler size of up to 16 microns in the prior art provides a relatively low surface area available for release. In contrast, nano-sized fillers of the present invention have surface areas 3.7-53 times higher, and hence the new composites of this invention, for example, release $Ca^{2+}$ and $PO_4$ with concentrations of 2 to 7 mmol/L and as high as 16 mmol/L.

Thus, it is an object of the invention to provide new dental and/or bone composite materials exhibiting strength and antibacterial or medicinal characteristics.

A further object of the invention is to provide such composites which enable controlled release of therapeutic materials in combination with materials in a resin matrix which enhance strength of the composite.

These and other objects, advantages and features of the invention are set forth herein.

BRIEF DESCRIPTION OF THE DRAWING

In the detailed description which follows, reference will be made to the drawing comprised of the following figures:

In FIG. 9A flexural strength (mean±sd; n=6) and in FIG. 9B fracture toughness (mean±sd; n=6) for the nano DCPA composites are significantly higher than the controls. The difference between SiC and $Si_3N_4$ is not statistically significant (Tukey's multiple comparison test; family confidence coefficient=0.95);

DESCRIPTION OF PREFERRED EMBODIMENTS

Figure 1A:
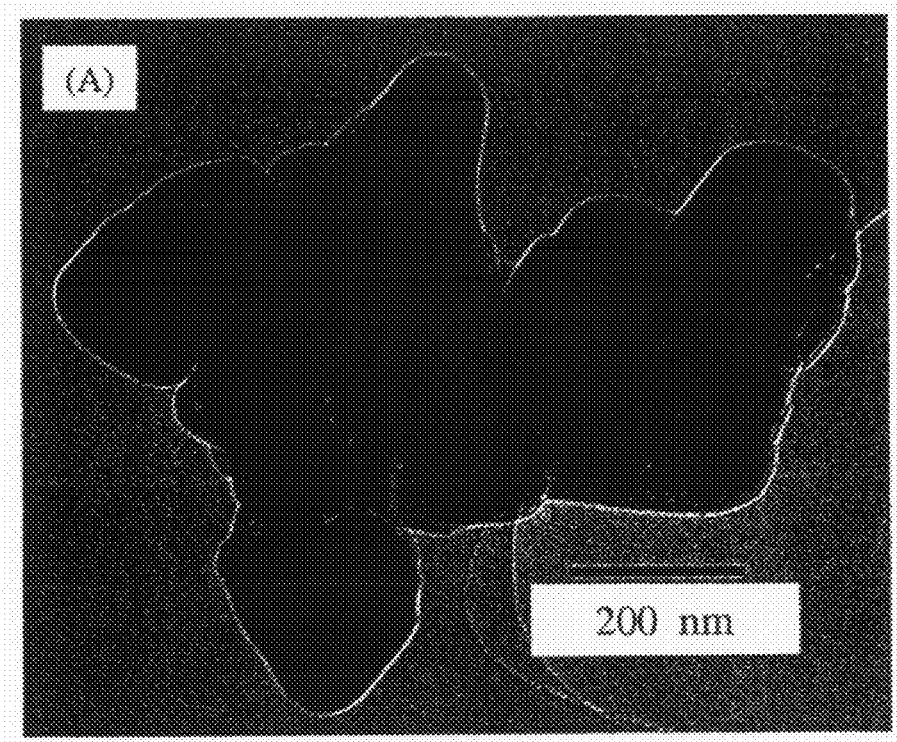
FIG. 1A is a transmission electron microscope (TEM) image for nano MCPM (monocalcium phosphate monohydrate, $Ca(H_2PO_4)_2 \cdot H_2O$) particles used to make nano dental materials.

The present invention relates to methods and compositions of new dental materials containing nano-sized calcium phosphate and other fillers to have calcium, phosphate, fluoride and other compound or material release including, but not limited to, potassium compounds, silver compounds, chloride compounds, antimicrobial materials, and others. This invention further relates to novel dental and/or bone compositions for restorations, stress-bearing applications, artificial crowns, anterior and posterior tooth fillings, adhesives, cavity liners, cements, bases, orthodontic devices, prostheses, and sealants. This invention further relates to methods and compositions for tailoring the releasing filler/strengthening filler ratio and the fast releasing filler/slow releasing filler ratio. This invention further relates to methods and compositions of fabricating high stress-bearing materials with substantial release of materials for the remineralization of decayed tooth structures.

The terms "nano" and "nano-sized" usually refer to sizes that range from 1 nm ($n=10^{-9}$, m=meter) to about $10^4$ nm, preferably from about 1 nm to $10^3$ nm. The term "fillers" refers to particles or elongated fibers that are filled into a material. The terms "silane" and "silanization" refer to a coating on the filler surface that bonds to a polymer matrix.

The terms "strengthener" and "strengthening fillers" refer to fillers that increase the strength and mechanical properties of a composite. Strengthener can be glasses, ceramics, polymers and mixtures thereof, in shapes of fibers, particulates, platelets or whiskers. The size of strengtheners ranges from 1 nm to 3 mm (1 mm=$10^{-3}$ m), preferably from 10 nm to 100 microns (1 micron=$10^{-6}$ m), and most preferably from 50 nm to 50 microns. Examples of strengtheners include:

Silicate-containing ceramics, including glass and quartz particles and fibers;

Single-crystalline ceramics including silicon nitride-containing ceramics and silicon carbide-containing ceramics in the forms of particles, whiskers and fibers;

Polycrystalline ceramics including alumina and zirconia in the forms of particles, whiskers and fibers;

Carbon fibers;

Polymer-based particles and fibers; and

Titanium fibers.

The terms "releaser" and "releasing fillers" refer to fillers that release calcium, phosphate and fluoride ions. The terms "hardenable", "cure", "polymerization" and related terms refer to a paste-like or liquid-like material being able to harden and form a solid. The term "monomer" refers to a liquid that can be hardened to form a polymer.

Various resins may be utilized, at least in part, as a matrix for fillers including the following:

Bis-GMA (bisphenol glycidyl methacrylate) based resins.

TEGDMA (triethylene glycol dimethacrylate) based resins.

HEMA (2-hydroxyethyl methacrylate) based resins.

PMDM (pryomellitic acid diethylmethacrylate) based resins.

PMGDM (pyromellitic acid glycerol dimethacrylate) based resins.

UDMA (urethane dimethacrylate) based resins.

Methacrylate based resins.

Dimethacrylate based resins.

Hydrophobic resins.

Hydrophilic resins.

Hardenable monomers suitable for dental applications.

The present invention will be further understood in view of the following examples, which are merely illustrative and not meant to limit the scope of the invention.

EXAMPLE 1

Nano MCPM particles. In this example, nano-sized MCPM (monocalcium phosphate monohydrate, $Ca(H_2PO_4)_2 \cdot H_2O$) particles are used as fillers to make dental releasing materials. The nano MCPM powder can be prepared by using a spray drying process or other suitable processes. The spray drying apparatus consists of a spray nozzle situated on the top of a glass column, which is heated with electrical heating tapes and thermally insulated. The water in the diluted Ca—P solution are evaporated into the dry, heated air in the column and expelled from the precipitator into a hood. The fine particles suspended in the flow are trapped in the precipitator and collected at the end of the process. The solution for making nano MCPM is prepared by dissolving $CaCO_3$ in a $H_3PO_4$ diluted solution (8 mM Ca and 16 mM $PO_4$). While this process serves as an example, nano MCPM from other processes can also be used as fillers for dental materials.

Figure 1B:
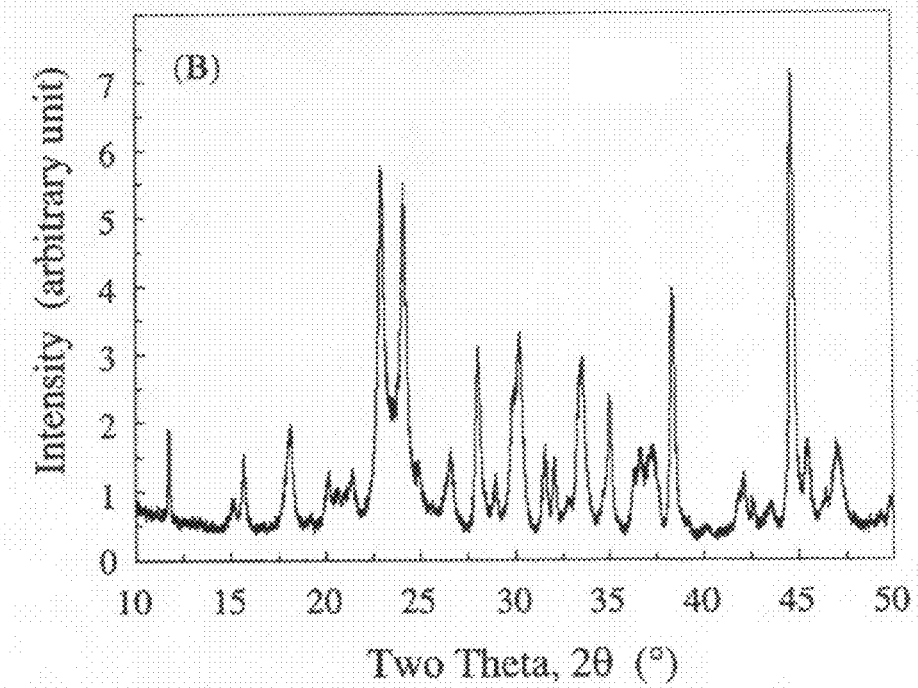
FIG. 1B is an x-ray diffraction (XRD) image for nano MCPM (monocalcium phosphate monohydrate, $Ca(H_2PO_4)_2 \cdot H_2O$) particles used to make nano dental materials.

Examples of nano MCPM particles thus produced are shown in the scanning electron micrograph (TEM) in FIG. 1A. The particle sizes range from approximately 100 nm to 200 nm. The nano particles are characterized using x-ray diffraction (XRD, Rigaku DMAX 2200, Rigaku Denki Co., Woodlands, Tex.) showing that they are MCPM (FIG. 1B).

EXAMPLE 2

Nano DCPA particles. In this example, nano-sized DCPA (dicalcium phosphate anhydrous, $CaHPO_4$) particles are used as fillers in dental materials. Nano DCPA can be made by using a method similar to that described in Example 1 as well as by other suitable methods. For nano DCPA, the solution being sprayed contains an acid component to solubilize the calcium phosphate compound. The DCPA-saturated solution that is used in the spray drying process is prepared by dissolving commercial DCPA in a dilute acetic acid (16 mmol/L) solution (8 mM Ca and $PO_4$). While this process serves as an example, nano DCPA from other processes can also be used as fillers for dental materials.

Figure 2A:
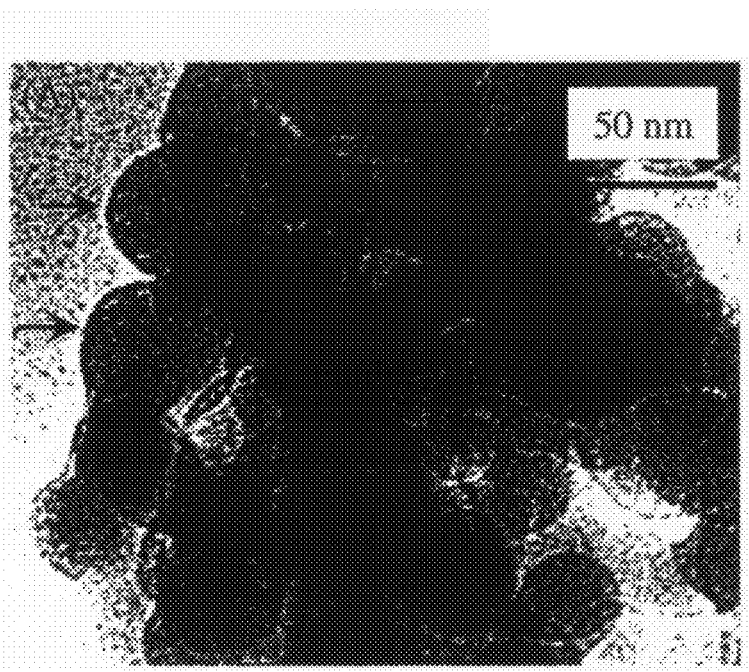
FIGS. 2A and 2B are respectively a TEM and XRD for nano DCPA (dicalcium phosphate anhydrous, $CaHPO_4$) particles used to make nano dental materials.
Figure 2B:
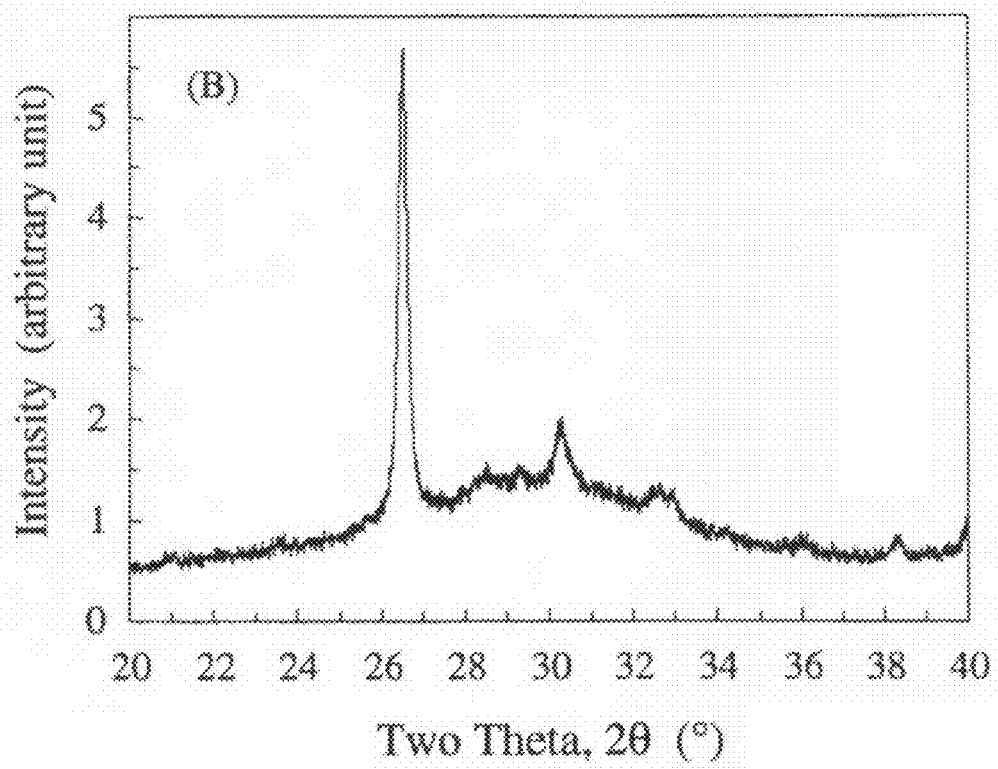

Examples of nano DCPA particles thus produced are shown in the TEM micrograph in FIG. 2A. The particle sizes range from about 50 nm to 200 nm. Some nano particles appear to be connected to form a fibrous structure. The thickness of the fibrous structure is about 50 nm, and the length of the fibrous structure is about 200 nm. The XRD result is plotted in FIG. 2B showing that these nano particles are poorly crystalline DCPA.

EXAMPLE 3

Direct-filling nano MCPM composites with HEMA. An example of manufacture of this invention comprises direct-filling composites containing nano MCPM and a strengthener. The strengthener can be glasses, ceramics, metals, polymers and mixtures thereof. They can be fibers, particulates or whiskers. As an example of using a strengthener, silicon carbide (SiC) fillers are used with an elongated shape having a diameter of 0.1-3 µm with a mean of 0.9 µm, and a length of 2-100 µm with a mean of 14 µm. SiC is mixed with silica ($SiO_2$) having a particle size of 40-70 nm, at a SiC:silica mass ratio of 5:1, to serve as an example. The mixed powder is heat-treated at a temperature of 800° C. for 30 min. The powder is silanized as usual by mixing it with mass fractions of 4% 3-methacryloxypropyltrimethoxysilane (MPTMS) and 2% n-propylamine in cyclohexane in a rotary evaporator. The silanized nano-silica-SiC fillers are referred to as SiC strengthener. The strengthener is mixed with nano MCPM fillers at strengthener:nano MCPM mass ratio of 1:0, 2:1, 1:1, 1:2 and 0:1.

Figure 3A:
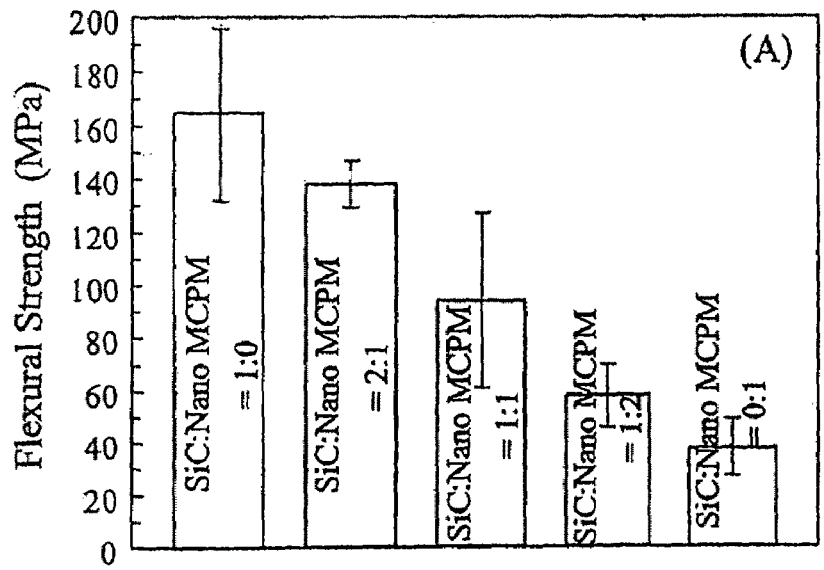
FIG. 3A is a bar graph depicting flexural strength of nano MCPM composites with strengthener:nano MCPM mass ratio of 1:0, 2:1, 1:1, 1:2, and 0:1. In this example, the strengthener is SiC. Each value is the mean of six measurements with the error bar showing one standard deviation (mean±sd; n=6)

Each powder is blended with a usual resin monomer consisting of mass fractions of 36.475% Bis-GMA (bisphenol glycidyl methacrylate), 36.475% TEGDMA (triethylene glycol dimethacrylate), 25% 2-hydroxyethyl methacrylate (HEMA), 0.05% 2,6-di-tert-butyl-4-methylphenol (BHT), and 2% benzoyl peroxide (BPO) to form paste one, the initiator paste, of a two-part chemically-activated composite. The filler level (SiC+nano MCPM)/(SiC+nano MCPM+resin) is 70% mass fraction. Paste two, the accelerator paste, consists of the same amount of powder mixed with a resin of mass fractions of 37% Bis-GMA, 37% TEGDMA, 25% HEMA, and 1% N,N-dihydroxyethyl-p-toluidine (DHEPT) as the polymerization accelerator. Equal masses of the two pastes are blended and filled into a 2 mm×2 mm×25 mm mold. Each specimen is chemically cured at 37° C. for 15 min, demolded, and incubated at 37° C. for 24 h prior to mechanical testing. For SiC:nano MCPM of 0:1, the filler level of 70% yields a paste that is relatively dry, hence a filler level of 60% is used. A three-point flexural test with a span of 10 mm is used to fracture the specimens at a crosshead speed of 1 mm/min. Flexural strength is plotted in FIG. 3A.

Figure 3B:
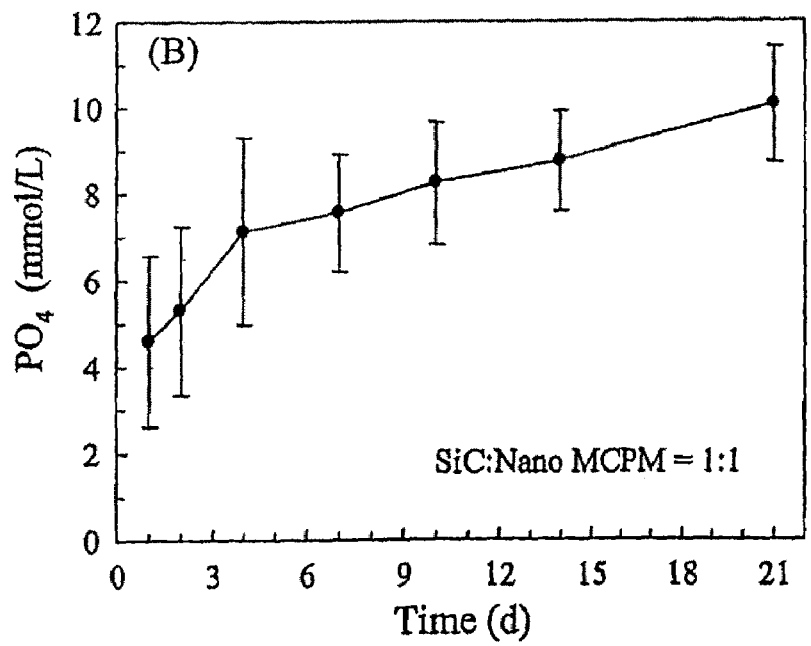
FIG. 3B is a graph of an example of $PO_4$ ion release versus immersion time for composite with strengthener:nano MCPM mass ratio of 1:1. Each value is mean±sd; n=3.

To measure calcium and phosphate release, composite specimens are cured and incubated at 37° C. for 1 d, and then immersed in NaCl solution buffered to a pH of 7.4. Aliquots of 0.5 mL are taken at regular time intervals, and analyzed for calcium ion ($Ca^{2+}$) and phosphate ion ($PO_4$) concentration by spectrophotometer. An example of a release profile is shown in FIG. 3B as a function of immersion time from 1 day (d) to 21 d.

Figure 4A:
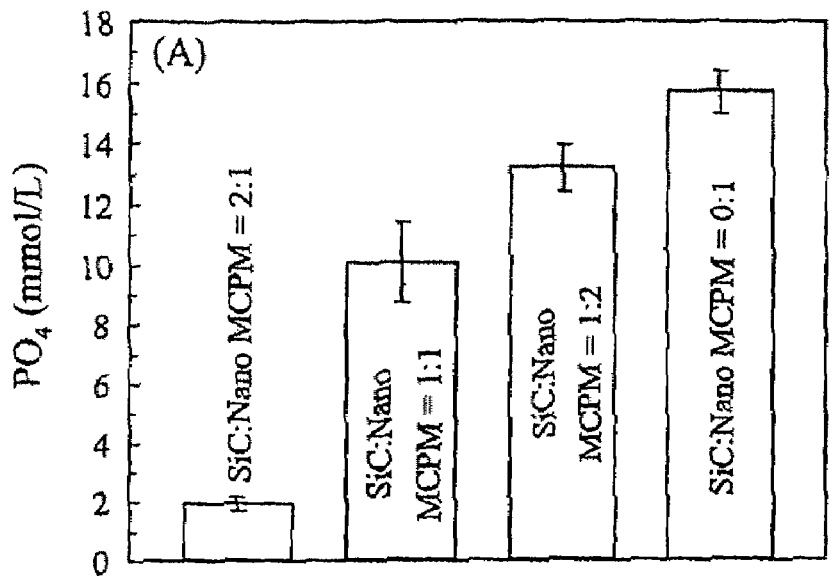
FIGS. 4A and 4B, respectively, are graphs of $PO_4$ and $Ca^{2+}$ ion release at 21 day immersion for four direct-filling composites at strengthener:nano MCPM mass ratios of 2:1, 1:1, 1:2 and 0:1, respectively. In this example, the resin contains HEMA (2-hydroxyethyl methacrylate), and the strengthener is SiC. Each value is mean±sd; n=3.
Figure 4B:
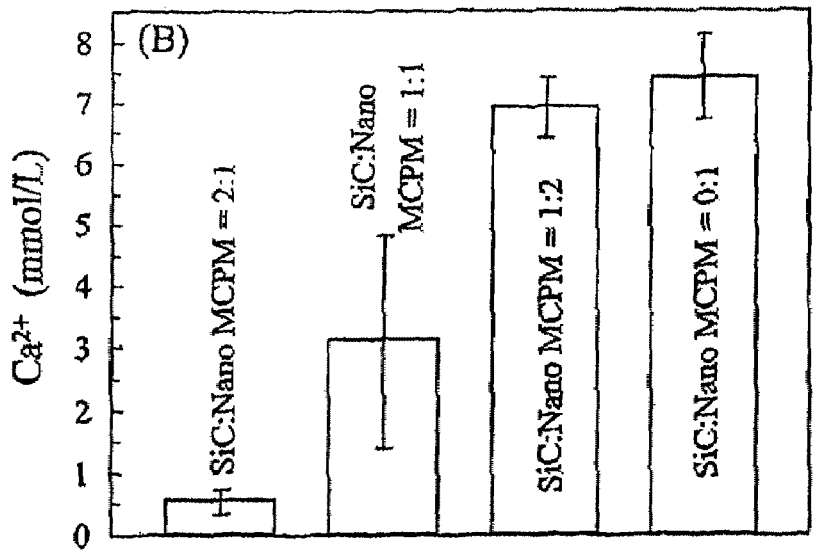

The release after 21 d of immersion is shown in FIG. 4. This figure includes four nano composites, at SiC:nano MCPM ratio of 2:1, 1:1, 1:2, and 0:1, respectively.

EXAMPLE 4

Effects of filler particle size. Another example of manufacture of this invention comprises composites with small filler particle sizes with high filler surface areas.

In the prior art (for example, Dickens et al., Dent Mater 19:558-566, 2003), tetracalcium phosphate (TTCP, $Ca_4(PO_4)_2O$) particles of size of 16 microns (=16,000 nm) and dicalcium phosphate anhydrous (DCPA, $CaHPO_4$) particles of size of 1.1 microns (1,100 nm) are used. The resin-based cement shows excellent usefulness in dental pulp capping applications. It releases cumulative calcium ions of about 0.3-1.0 mmol/L and phosphate ions of 0.05-0.5 mmol/L, after 90 d immersion.

In other prior art, novel amorphous calcium phosphate dental composite with excellent remineralizing properties releases calcium ions of 0.25-1.2 mmol/L and phosphate ions of 0.25-0.8 mmol/L (Skrtic et al., Dent Mater 12:295-301, 1996; Skrtic et al., J Biomed Mater Res (Appl Biomater) 53:381-391, 2000).

In the present invention (FIG. 4), calcium ion release of 3-7 mmol/L and phosphate ion release of 10-16 mmol/L are achieved, at 21 d immersion. The comparisons with prior art is listed in the table below.

| Materials | $PO_4$ (mmol/L) | $Ca^{2+}$ (mmol/L) |
|---|---|---|
| Nano composites of this invention (FIG. 4) | 10-16 | 3-7 |
| Dental cements of prior art (Dickens et al., Dent Mater 19: 558-566, 2003) | 0.05-0.5 | 0.3-1.0 |
| Dental composites of prior art (Skrtic et al., Dent Mater 12: 295-301, 1996; Skrtic et al., J Biomed Mater Res (Appl Biomater) 53: 381-391, 2000) | 0.25-0.8 | 0.25-1.2 |

For the purpose of illustration, use an average nano particle size of 300 nm. The particle surface area is increased by 3.7-fold compared to a particle size of 1.1 microns. The particle surface area is increased by 53-fold compared to a particle size of 16 microns. While the calcium phosphate compositions may also influence the release, this example shows the critical importance of using nano-sized fillers to dramatically increase the surface area and the amount of calcium and phosphate ion release for dental composites.

EXAMPLE 5

Figure 5A:
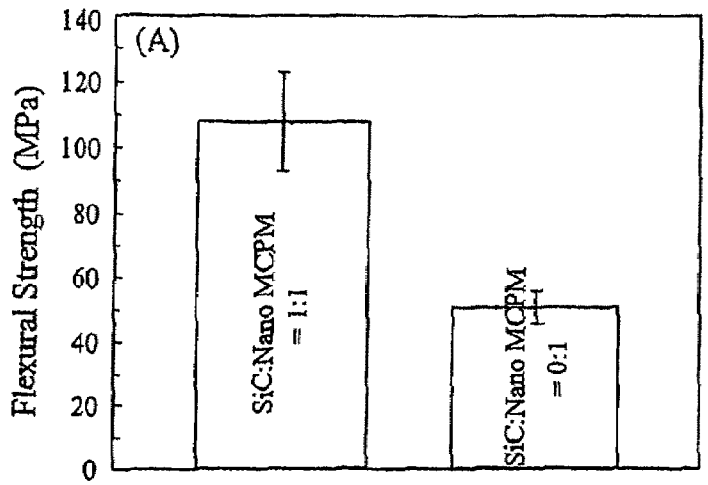
FIGS. 5A, 5B and 5C, respectively, are bar graphs depicting flexural strength of direct-filling nano MCPM composite. $PO_4$ and $Ca^{2+}$ ion release data at 21 d immersion, respectively. Each value is mean±sd; n=3. For FIG. 5A, the resin contains no HEMA, and the strengthener is SiC. Each value is mean±sd; n=6.
Figure 5B:
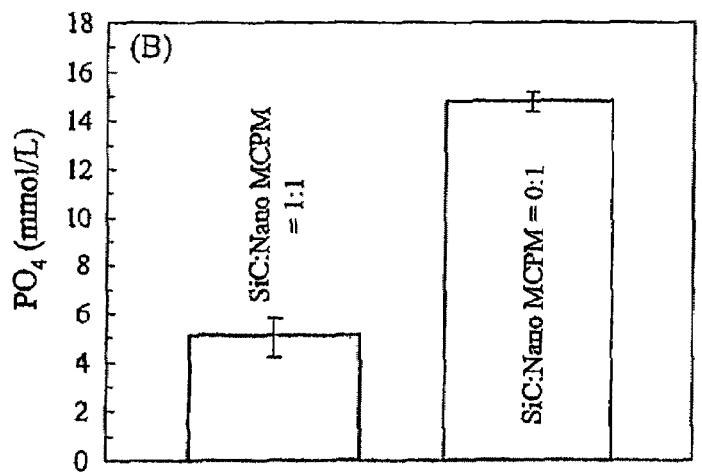
Figure 5C:
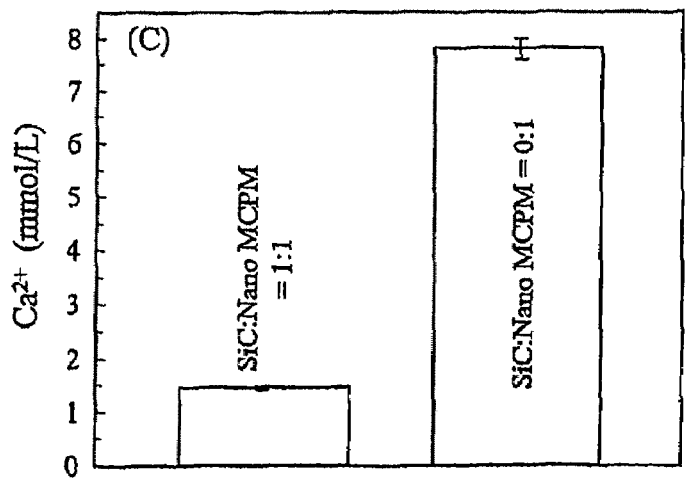

Direct-filling nano MCPM composites without HEMA. Another example comprises composites containing nano MCPM using a two-part chemically cured resin without HEMA. The SiC:nano MCPM mass ratios are 1:1 and 0:1. The initiator monomer consists of mass fractions of 48.975% Bis-GMA, 48.975% TEGDMA, 0.05% BHT, and 2% BPO. The accelerator resin consists of 49.5% Bis-GMA, 49.5% TEGDMA, and 1% DHEPT. The flexural strength results are plotted in FIG. 5A. The $PO_4$ and $Ca^{2+}$ ion release after 21 d of immersion are plotted in FIGS. 5B and 5C, respectively.

EXAMPLE 6

Figure 6A:
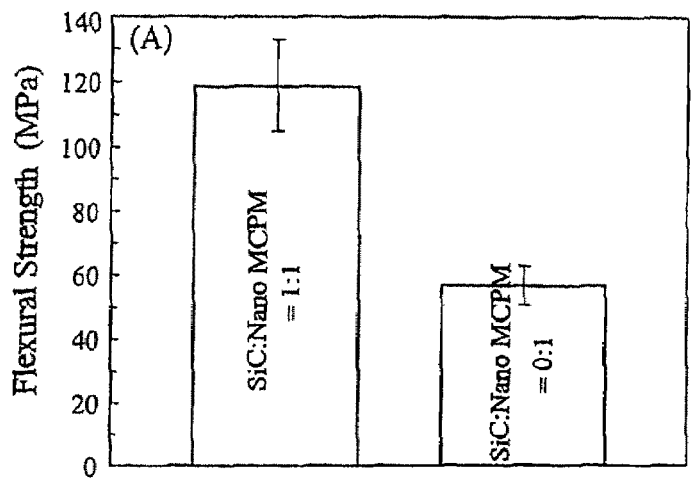
FIG. 6A depicts flexural strength of indirect nano MCPM composites. In this example, the strengthener is SiC, and each value is mean±sd; n=6.
Figure 6B:
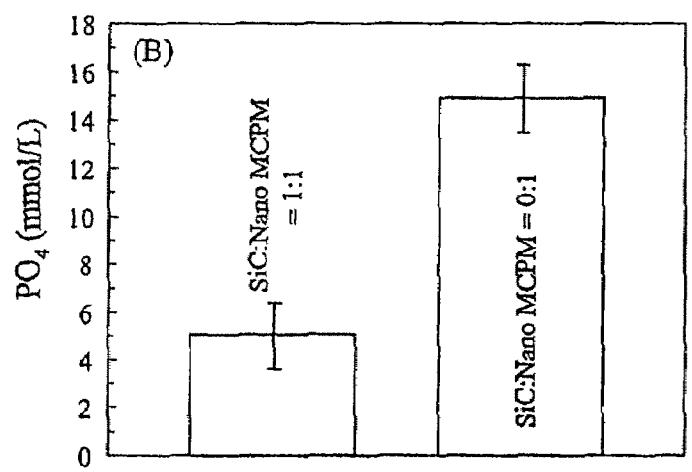
FIGS. 6B and 6C depict $PO_4$ and $Ca^{2+}$ ion release at 21 d immersion, respectively. Each value is mean±sd; n=3.
Figure 6C:
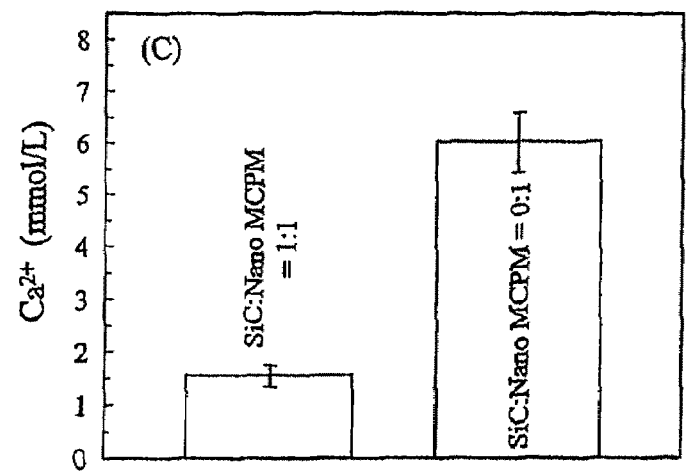

Indirect nano MCPM composites. Another example comprises composites containing nano MCPM for indirect restorations. The SiC:nano MCPM mass ratios are 1:1 and 0:1. The monomer consists of mass fractions of 48.965% of Bis-GMA, 48.965% TEGDMA, 2% BPO, and 0.07% 4-methoxylphenol (MEHQ). The paste is placed into a steel mold of 2 mm×2 mm×25 mm, and heat-cured in an oven at 140° C. for 30 min at room atmospheric pressure. The strength is plotted in FIG. 6A. The $PO_4$ and $Ca^{2+}$ ion release after 21 d are shown in FIGS. 6B and 6C, respectively.

EXAMPLE 7

Figure 7A:
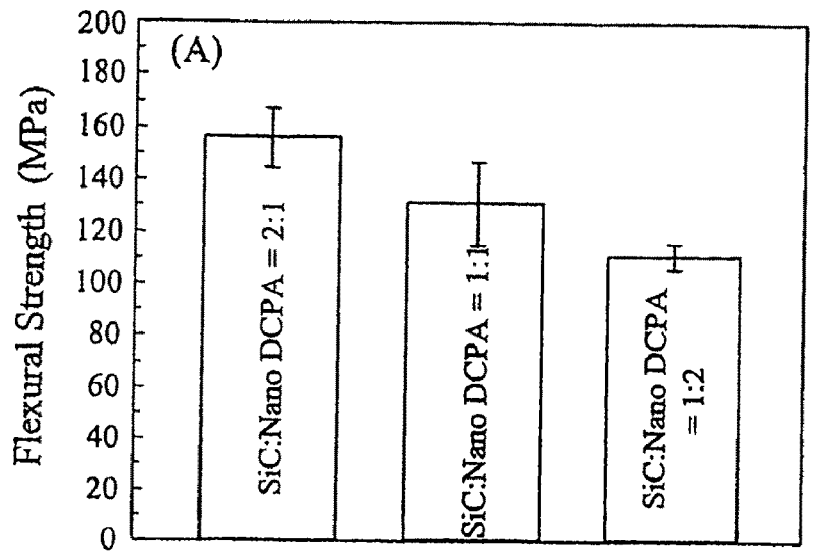
FIG. 7A is a bar graph depicting nano DCPA direct-filling composites at strengthener:nano DCPA mass ratio of 2:1, 1:1, and 1:2. In this example, the resin contains HEMA and the strengthener is SiC. Each value is mean±sd; n=6.

Direct-filling nano DCPA composites with HEMA. Another example comprises composites using nano DCPA. SiC:nano DCPA mass ratios of 2:1, 1:1, and 1:2 are used. Direct-filling composites are made using two-part chemically-cured resin with HEMA. Specimens are fabricated and incubated at 37° C. for 24 h. Flexural strength is plotted in FIG. 7A.

Figure 7B:
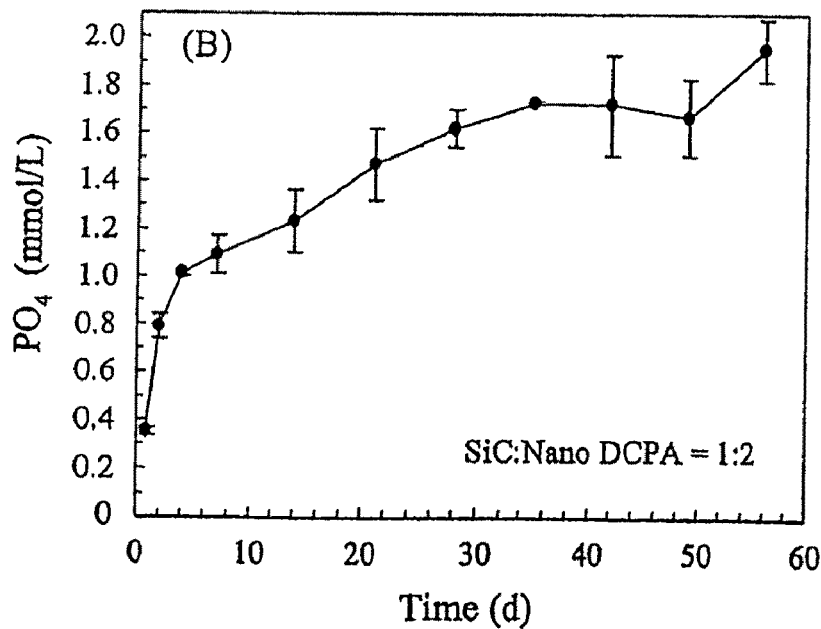
FIG. 7B is a graph depicting an example of $PO_4$ release over time (d) for nano DCPA composite at strengthener:nano DCPA ratio of 1:2. Each value is mean±sd; n=3.

As an example, $PO_4$ release is shown in FIG. 7B. Release of phosphate ions at 56 d (mean±sd; n=3, where sd=standard deviation, n=number of repeats) is measured to be (1.95±0.13) mmol/L, (0.98±0.05) mmol/L, and (0.48±0.08) mol/L, at SiC:nano DCPA ratios of 1:2, 1:1 and 2:1, respectively. Release of calcium ions is (0.68±0.07) mmol/L, (0.38±0.05) mmol/L, and (0.21±0.02) mol/L, respectively.

EXAMPLE 8

Direct-filling nano DCPA composites without HEMA. Another example comprises composites using nano DCPA and a resin without HEMA. In this example, SiC:nano DCPA mass ratios of 2:1, 1:1, and 1:2 are used. Direct-filling composites are made using two-part chemically-cured resin. Flexural strength, $PO_4$ and $Ca^{2+}$ ion release (at 56 d of immersion) are listed in the table below.

| SiC:Nano DCPA Ratio | Flexural Strength (MPa) | $PO_4$ (mmol/L) | $Ca^{2+}$ (mmol/L) |
|---|---|---|---|
| 2:1 | 148 ± 9 | 0.34 ± 0.01 | 0.17 ± 0.01 |
| 1:1 | 123 ± 11 | 0.997 ± 0.001 | 0.38 ± 0.01 |
| 1:2 | 110 ± 13 | 1.58 ± 0.04 | 0.40 ± 0.01 |

EXAMPLE 9

Indirect nano DCPA composites. Another example would be to make indirect composites using nano DCPA and a heat-cured resin. In this example, SiC:nano DCPA mass ratios of 2:1, 1:1, and 1:2 are used. Flexural strength, $PO_4$ and $Ca^{2+}$ ion release (at 56 d of immersion) are listed in the table below.

| SiC:Nano DCPA Ratio | Flexural Strength (MPa) | $PO_4$ (mmol/L) | $Ca^{2+}$ (mmol/L) |
|---|---|---|---|
| 2:1 | 167 ± 23 | 0.31 ± 0.03 | 0.17 ± 0.01 |
| 1:1 | 153 ± 20 | 0.95 ± 0.01 | 0.41 ± 0.01 |
| 1:2 | 137 ± 18 | 1.57 ± 0.06 | 0.45 ± 0.07 |

EXAMPLE 10

Fillers of different calcium and phosphate compositions. Another example comprises dental materials using various types of calcium and phosphate fillers. This includes monocalcium phosphate monohydrate (MCPM: $Ca(H_2PO_4)_2 \cdot H_2O$), dicalcium phosphate anhydrous (DCPA: $CaHPO_4$), tetracalcium phosphate (TTCP: $Ca_4(PO_4)_2O$), alpha-tricalcium phosphate ($\alpha\text{-}Ca_3[PO_4]_2$), calcium carbonate ($CaCO_3$), beta-tricalcium phosphate ($\beta\text{-}Ca_3[PO_4]2$), hydroxyapatite (HA, $Ca_5[PO_4]_3OH$), carbonated HA, calcium-deficient HA, poorly crystalline HA, dicalcium phosphate dihydrate (DCPD, $CaHPO_4 \cdot 2H_2O$), amorphous calcium phosphate-based materials (the term amorphous refers to the material being not crystalline or being poorly crystalline), calcium hydroxide ($Ca(OH)_2$, calcium fluoride ($CaF_2$), and combinations thereof.

EXAMPLE 11

Calcium and phosphate fillers of different sizes and morphologies. Another example comprises dental materials using calcium and phosphate fillers of different sizes and morphologies. The filler sizes can range from 1 nm to $10^5$ nm, preferably from 10 nm to $10^4$ nm, most preferably from 50 nm to $10^3$ nm. The filler morphologies include particulates and fibers. Combinations of fillers of different sizes and morphologies can also be used.

EXAMPLE 12

Tailoring the release rates. Another example would be to combine nano calcium and phosphate fillers with different release rates. This includes combining fast dissolution nano calcium phosphate fillers with slower dissolution calcium phosphate fillers, or combining acidic calcium phosphates with basic calcium phosphates. Such examples include combining nano MCPM with DCPA, DCPA with TTCP, DCPA with DCPD, DCPA with calcium fluoride, DCPA with HA, or MCPM with HA.

The second part of this example is to tailor the release rate through pH changes in the environment. For example, a dental material filled with nano HA or DCPA particles has less ion release at pH=7, and more release at pH of 5 or 4. A low pH simulates the oral environment that causes tooth decay, when an increased release of ions is most needed.

EXAMPLE 13

Tailoring the amount of release and the stress-bearing ability. Another example comprises tailoring the amount of release by varying the strengthener to releaser ratio. Because the nano calcium and phosphate particles produce a high level of release, it becomes feasible to increase the strengthener filler level and vary the releasing filler/strengthening filler ratio. Thus, composites with high stress-bearing capabilities and sufficient ion releases can be produced.

The types of strengtheners include ceramics, glasses, metals, polymers, and combinations thereof. The strengthener filler size ranges from 1 nm to 10 mm, preferably from 10 nm to 100 microns, most preferably from 50 nm to 50 microns. For example, glass particles of 0.1 micron to 10 microns can be used, and glass fibers and quartz fibers of several microns in diameter and several mm in length can also be used as strengthening fillers. Hence the morphologies and shapes of strengtheners include whiskers, fibers, fibrous structures, particulates, and combinations thereof.

EXAMPLE 14

Dental materials with fluoride ($F^-$) release. Another example comprises dental materials with fluoride ($F^-$) ion release. For example, calcium fluoride ($CaF_2$) nano fillers can be incorporated in the composite. Other fillers include various calcium and phosphate compounds, fluoride-containing glasses, glass ionomer-based materials and fillers, ion-releasing fluorosilicate glass fillers, glass ionomer particles, and resin-modified glass ionomer particles. Strengtheners can also be included in the composite.

Figure 8A:
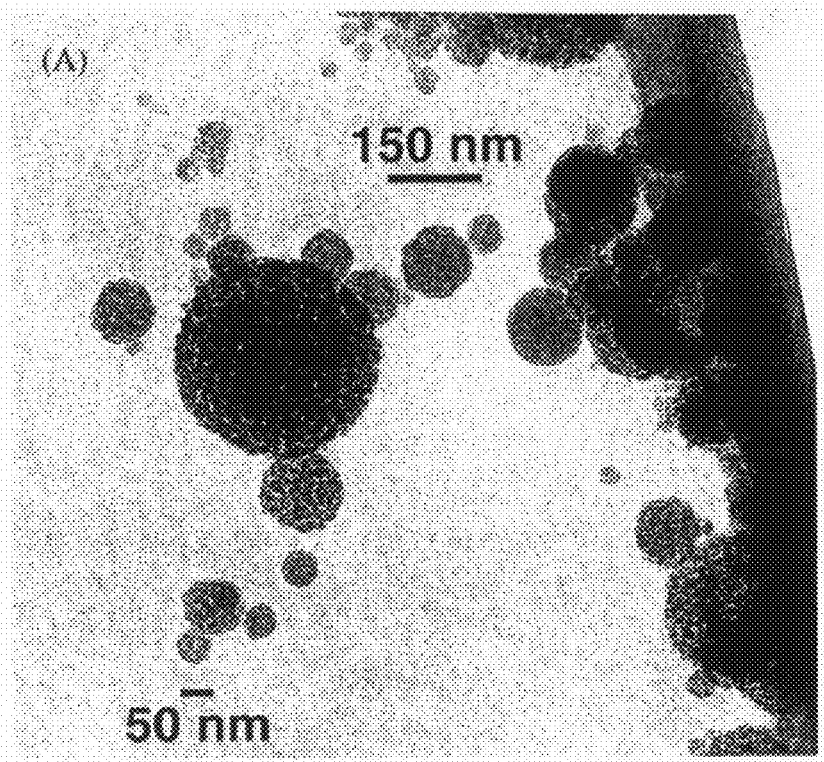
FIGS. 8A and 8B, respectively, are TEM and XRD for nano $CaF_2$ particles used to make nano dental materials.
Figure 8B:
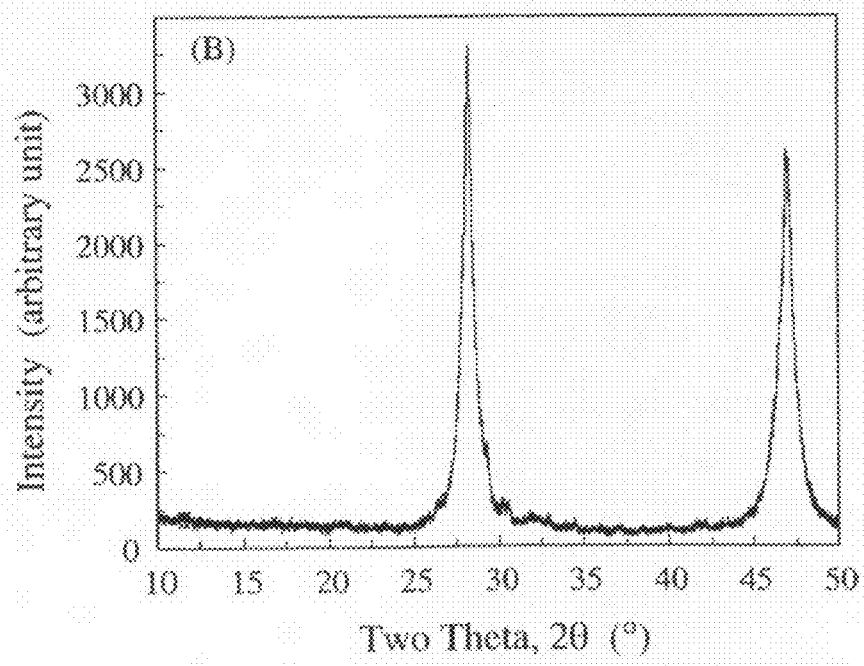

As an example, a direct-filling composite is made by using two-part chemical curing, with a total filler level of 65% mass fraction. The fillers include 20% mass $CaF_2$ nano particles for $F^-$ ion release, 20% mass of DCPA, and 25% mass of silicon nitride whiskers as strengtheners. Examples of the $CaF_2$ particles are shown in FIG. 8A, with its XRD pattern in FIG. 8B. The nano $CaF_2$ particle diameter ranges from about 50 nm to 300 nm.

Specimens are fabricated in 2 mm×2 mm×25 mm molds. Each specimen is incubated at 37° C. for 24 h prior to mechanical testing. The flexural strength for this new nano composite is measured (mean±sd; n=5) to be (99.5±7.2) MPa. It is higher than a reported flexural strength of 10-20 MPa for previous fluoride-releasing glass ionomers (McLean, J Am Dent Assoc 120:43, 1990) and 60 MPa for resin-based glass ionomer materials (Poolthong et al., Dent Mater J 13:220, 1994).

EXAMPLE 15

Effects of compositions and curing methods on nano releasing materials. Another example comprises materials with different compositions, using various polymers and curing methods. In this example, nano DCPA particles are used with a SiC:nano DCPA ratio of 2:1 and a total filler mass fraction of 60%. Different hardenable or curable polymers, various methacrylate-containing materials and dimethacrylate-containing materials, hydrophobic monomers and hydrophilic monomers, can be used. The methods of hardening include chemical curing, light curing, heat curing, pressure curing, or mixtures thereof. As an example, three different resins are used here.

Resin 1 consists of 48.965% of Bis-GMA, 48.965% TEGDMA, 2% BPO, and 0.07% MEHQ; it is heat cured at 140° C. for 30 min.

Resin 2 is two-part chemically cured, with the first part consisting of 48.975% Bis-GMA, 48.975% TEGDMA, 0.05% BHT, and 2% BPO, and the second part consisting of 49.5% Bis-GMA, 49.5% TEGDMA, and 1% DHEPT.

Resin 3 is two-part chemically cured, with the first part comprising of 36.475% Bis-GMA, 36.475% TEGDMA, 25% HEMA, 0.05% BHT and 2% BPO, and the second part comprising of 37% Bis-GMA, 37% TEGDMA, 25% HEMA, and 1% DHEPT.

Three composites without calcium and phosphate are also tested. The paste of an indirect laboratory composite (Concept, Ivoclar North America, Amherst, N.Y.) is cured in the Concept Heat Integrated Processor at 120° C. for 10 min under a pressure of 0.6 MPa. It is referred to as inlay/onlay control. It consists of a mass percentage of 76% silicate fillers in a urethanedimethacrylate resin. The paste of a second indirect laboratory composite (Artglass, Heraeus Kulzer GmbH, Wehrheim, Germany) is cured in a Dentacolor XS photo-curing unit for 90 seconds on each side of the specimen. It is referred to as prosthetic control. It has a filler mass fraction of 70%. The third control is a direct-filling composite containing nano silica with a diameter of 40-80 nm at a filler level of 50%.

Specimens are fabricated in 2 mm×2 mm×25 mm molds. Each specimen is incubated at 37° C. for 24 h prior to mechanical testing. The flexural strength is listed in the table below. For release test, specimens are cured and immersed in NaCl solution buffered to pH=7.4. $Ca^{2+}$ concentration is measured via atomic absorption spectroscopy, and $PO_4$ concentration is measured using a spectrophotometer. The $Ca^{2+}$ and $PO_4$ ion releases at 14 d of immersion are also listed in the table below.

| Composite | Flexural Strength (MPa) | $PO_4$ (mmol/L) | $Ca^{2+}$ (mmol/L) |
|---|---|---|---|
| Nano DCPA composite, indirect, heat-cured | 167 ± 23 | 0.20 ± 0.02 | 0.17 ± 0.01 |
| Nano DCPA composite, direct filling, no HEMA | 148 ± 9 | 0.20 ± 0.01 | 0.17 ± 0.01 |
| Nano DCPA composite, direct filling, with HEMA | 156 ± 11 | 0.30 ± 0.07 | 0.21 ± 0.02 |
| Inlay/onlay control | 120 ± 16 | No release | No release |
| Prosthetic control | 123 ± 21 | No release | No release |
| Nano composite control | 83 ± 14 | No release | No release |

The novel nano DCPA composites, with $Ca^{2+}$ and $PO_4$ ion release, have significantly (Tukey's multiple comparison test; family confidence coefficient=0.95) higher strength than the control composites without $Ca^{2+}$ and $PO_4$ release.

EXAMPLE 16

Dental bonding agents/adhesives with ion release. Another example comprises dental bonding agents and adhesives with releasing nano fillers. A SiC:nano DCPA ratio is 2:1. As an example, a filler level of 40% by mass is used to result in a relatively liquid-like paste. For direct-filling applications, the pastes are two-part chemically cured to make specimens of 2 mm×2 mm×25 mm. Specimens are incubated at 37° C. for 24 h prior to mechanical testing. The flexural strength (mean±sd; n=6) is measured to be (104±15) MPa.

The $Ca^{2+}$ release at 35 d of immersion is (0.09±0.02) mmol/L, and the $PO_4$ release is (0.11±10.01) mmol/L.

EXAMPLE 17

Dental crown cements with $Ca^{2+}$ and $PO_4$ release. Another example comprises dental crown cements containing releasing nano fillers. A SiC:nano DCPA ratio is 2:1. As an example, a filler level of 50% by mass is used to result in a flowable paste. For direct-filling applications, the pastes are two-part chemically cured to make specimens of 2 mm×2 mm×25 mm. Specimens are incubated at 37° C. for 24 h prior to mechanical testing. The flexural strength (mean±sd; n=6) is measured to be (105±12) MPa.

The $Ca^{2+}$ release at 35 d of immersion is (0.15±0.04) mmol/L, and the $PO_4$ release is (0.25±0.03) mmol/L.

EXAMPLE 18

Orthodontic bracket cements with $Ca^{2+}$ and $PO_4$ release. Another example comprises dental orthodontic bracket cement containing releasing nano fillers. The SiC:nano DCPA ratio is 2:1. As an example, a filler level of 60% by mass is used to result in a slightly flowable paste. For direct-filling applications, the pastes are two-part chemically cured. Specimens are incubated at 37° C. for 24 h prior to mechanical testing. Flexural strength (mean±sd; n=6) is (148±9) MPa.

The $Ca^{2+}$ release at 56 d of immersion is (0.383±0.001) mmol/L, and the $PO_4$ release is (0.997±0.001) mmol/L.

EXAMPLE 19

Light-cured composite with ion release using glass fiber as strengthener. Another example comprises light-cured releasing nano composites. In this example, the strengthener is glass fibers (E-glass, Owens Corning Fiberglass, Columbus, Ohio). The fibers are discontinuous with a length of approximately 8 mm, and the fiber diameter is 16 microns. The strengthener:nano DCPA ratio is 1:1 and the total filler level is 50% mass fraction. The fillers are mixed with a dental rein of Bis-GMA and TEGDMA at 1:1 mass ratio, photo-activated with mass fractions of 0.2% camphorquinone and 0.8% ethyl 4-N,N-dimethylaminobenzoate. The specimen of 2 mm×2 mm×25 mm is cured using visible light (Triad 2000, Dentsply International, York, Pa.) for 1 min on each of two sides. The specimens are incubated at 37° C. for 24 h and then tested. The flexural strength (mean±sd; n=8) is listed in the table below along with a commercial inlay/onlay control and a prosthetic control.

| Material | Light-cured nano DCPA composite | Inlay/onlay control | Prosthetic control |
|---|---|---|---|
| Flexural strength (MPa) | 528 ± 25 | 120 ± 16 | 123 ± 21 |

It should be noted that the nano DCPA composite is light-cured and capable of direct-filling restorations with DCPA to release $Ca^{2+}$ and $PO_4$ ions. The control composites, with no such release, are indirect and require laboratory fabrication.

EXAMPLE 20

Light-cured dental releasing nano composite. Another example comprises light-cured nano composites containing nano DCPA and nano silica. In this example, silica ($SiO_2$) with a particle size of 40 nm to 80 nm is used and the silica:DCPA ratio is 2:1. The total filler level is 50% mass fraction. The fillers are mixed with a dental rein of Bis-GMA and TEGDMA at 1:1 mass ratio, photo-activated with mass fractions of 0.2% camphorquinone and 0.8% ethyl 4-N,N-dimethylaminobenzoate. The specimen of 2 mm×2 mm×25 mm is cured using visible light (Triad 2000, Dentsply International, York, Pa.) for 1 min on each of two sides. The specimens are incubated at 37° C. for 24 h and then tested. The flexural strength (mean±sd; n=6) is measured to be (82±8) MPa.

EXAMPLE 21

Figure 9A:
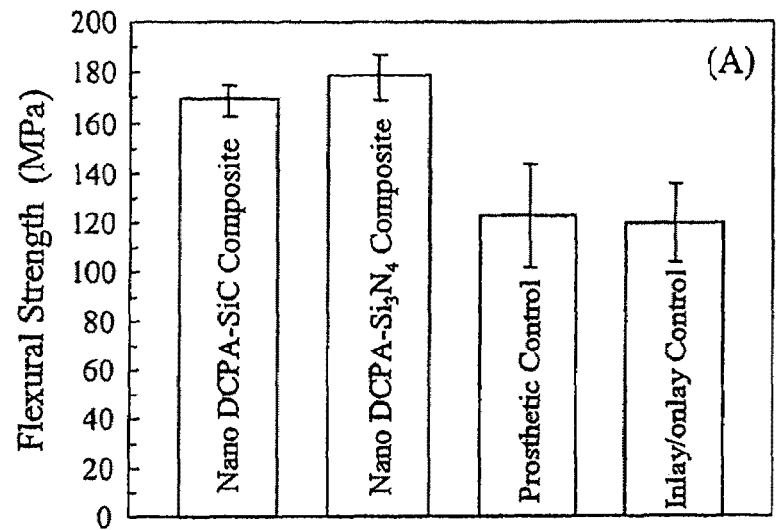
FIGS. 9A and 9B are bar graphs depicting strength for two different types of strengtheners used to develop nano DCPA composites with high strength and fracture toughness. In this example, the two strengtheners are SiC and $Si_3N_4$, and a strengthener:nano DCPA ratio of 2:1 is used. A filler level of 74% is used and the specimens are heat cured.

Releasing nano materials with different types of strengtheners. Another example comprises releasing nano composites by using different types of strengtheners. In this example, two different strengtheners are used, SiC and silicon nitride ($Si_3N_4$). A strengthener:nano DCPA ratio of 2:1 is used to have calcium and phosphate ion release. A filler level of 74% by mass is used and the specimens are heat cured. The flexural strength (mean±sd; n=6) is plotted in FIG. 9A for the new nano DCPA composites along with an inlay/onlay control and a prosthetic control. The control composites have no $Ca^{2+}$ or $PO_4$ release. The nano DCPA composites have significantly higher strength than the controls; the difference between SiC and $Si_3N_4$ is not significant (Tukey's at 0.95).

EXAMPLE 22

Figure 9B:
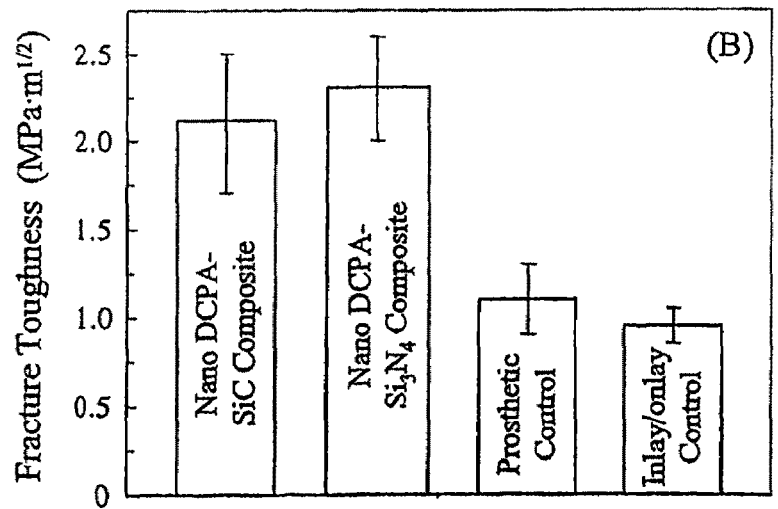

Releasing nano composites with high fracture toughness. Another example comprises releasing nano composites with high fracture toughness. Two strengtheners are used, SiC and $Si_3N_4$ fillers. A strengthener:nano DCPA ratio of 2:1 is used to have calcium and phosphate release. A filler level of 74% by mass is used and the specimens are heat cured. Fracture toughness (the material's resistance to crack propagation) is measured by using a usual single-edge-notched-beam method. A notch depth of approximately 700 microns is machined into a specimen of 2 mm×2 mm×25 mm by using a 150-micron thick diamond blade. Fracture toughness (mean±sd; n=6) is measured and plotted in FIG. 9B for the nano DCPA composites and two controls. The nano DCPA composites have significantly higher fracture toughness than the controls; the difference between SiC and $Si_3N_4$ is not significant (Tukey's at 0.95).

EXAMPLE 23

Releasing nano composites with high wear resistance. Another example comprises releasing nano composites with high resistance to occlusal wear. In this example, $Si_3N_4$ strengtheners are used. A strengthener:nano DCPA ratio of 2:1 is used to have calcium and phosphate ion release. A filler level of 74% by mass is used and the specimens are heat cured. A commercial indirect prosthetic composite (Artglass, Heraeus Kulzer GmbH, Wehrheim, Germany) is used as a control. The wear specimens are tested in a four-station wear testing apparatus (Caulk/Dentsply, Milford, Del.) for three-body occlusal wear. Each specimen is surrounded by a brass ring filled with a water slurry polymethyl methacrylate (PMMA) beads which served as simulated food slurry. A hardened carbide steel pin with a tip diameter of 3 mm is loaded onto the specimen. In each wear cycle, the pin is pressed down against the PMMA particles on the specimen surface and rotated 30 degrees. Upon reaching a maximum load of 76 N, the pin is counter-rotated during unloading and moved upward back to its original position. This wear cycle is repeated to a total of 400,000 cycles. The diameter and depth of the wear scars are measured by using a computer-controlled profilometer (Perthometer Concept, Mahr, Cincinnati, Ohio) with a diamond stylus of 5 μm tip radius. The maximum diameter and depth of the wear scars are measured with the unworn surface of the specimen as the baseline.

The results are listed in the table below, showing no significant difference between the two materials (p>0.1). The new nano DCPD composite with calcium and phosphate release has matched the wear resistance of a commercial indirect prosthetic composite with no calcium and phosphate release.

| Material | Wear Scar Depth (microns) | Wear Scar Diameter (microns) |
| --- | --- | --- |
| New Nano Composite | 177 ± 30 | 1027 ± 202 |
| Indirect Prosthetic Control | 173 ± 15 | 1184 ± 34 |

Current releasing composites do not possess such wear resistance.

EXAMPLE 24

Dental primers and adhesive resins for bonding to tooth dentin. Another example comprises releasing nano-filled adhesive systems. Primers refer to adhesion promoting agents that contain hydrophilic monomers dissolved in organic solvents such as acetone and ethanol. They serve the purpose of priming the dentinal surface layer and make the heterogeneous and hydrophilic dentin more receptive to bonding. Adhesive resins, also termed bonding agents, refer to mixtures of hydrophobic monomers, such as Bis-GMA and urethane dimethacrylate (UDMA), and more hydrophilic monomers, such as TEGDMA as a viscosity regulator and HEMA as a wetting agent. They serve the purpose of bonding a restoration to a tooth structure.

For dentin bonding, human third molar teeth are used. A usual 30% $H_3PO_4$ gel is applied to prepared dentin for 15 seconds (s). The dentin is rinsed with distilled water and then gently dried with a stream of air. The dentin is kept moist with a wet tissue paper. As control, one coat of a HEMA-containing primer (3M ESPE, St. Paul, Minn.) is first applied, then a Bis-GMA and HEMA containing adhesive resin (3M ESPE, St. Paul, Minn.) is applied and light-cured for 10 s. A resin composite (TPH, Caulk/Dentsply, Milford, Del.) is placed on top of the adhesive resin and light-cured for 60 s. Six teeth are thus bonded using the control adhesive resin, and another six teeth are bonded using the adhesive resin filled with nano DCPA particles to a filler level of 40% by mass.

Figure 10:
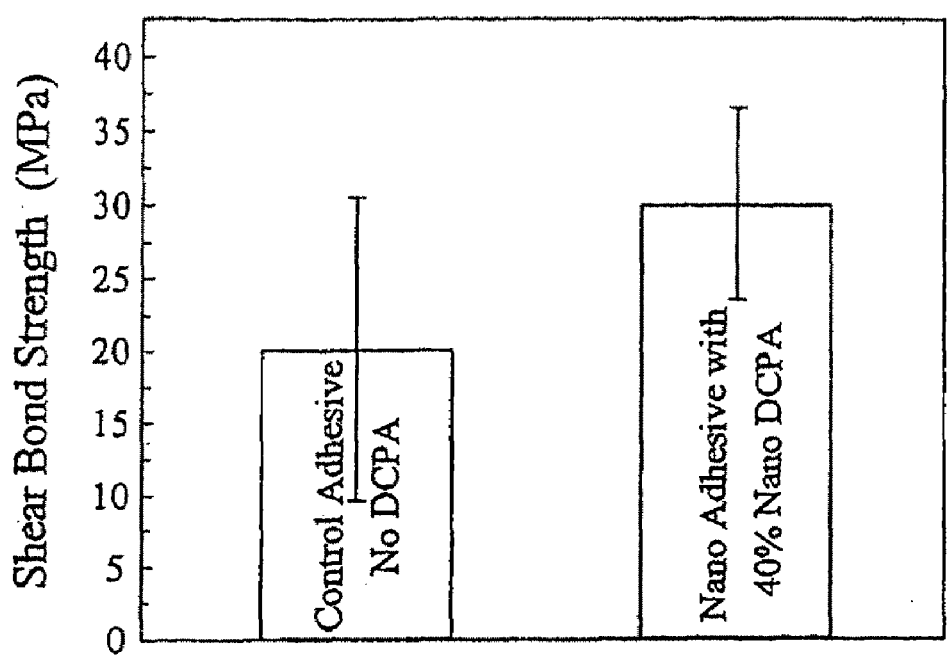
FIG. 10 is a bar graph depicting shear bond strength (MPa) of a control adhesive and a nano adhesive filled with 40% nano DCPA particles. Each value is mean±sd; n=6. The nano DCPA adhesive, with $Ca^{2+}$ and $PO_4$ release, increases the mean shear bond strength from 20.0 MPa for the control to 29.9 MPa for the nano adhesive.

After immersion in distilled water at 37° C. for 24 h, the bond is fractured in a shear bond test by applying a load at a displacement rate of 0.5 mm/min. The results are plotted in FIG. 10. Incorporating nano DCPA fillers to the adhesive resin, which imparts ion release, does not compromise the shear bond strength (p=0.076).

EXAMPLE 25

Dental adhesive resins for bonding to tooth enamel. Another example comprises adhesives to bond to enamel. Adhesive resins such as those containing Bis-GMA and TEGDMA with or without HEMA can be used. The adhesive resin can be filled with nano releasing fillers, for example, nano DCPA, $CaF_2$, HA, TTCP, and other calcium or phosphates. The filler level by mass for the adhesive resin ranges from 1% to 80%, preferably from 15% to 70%, most preferably from 30% to 60%.

EXAMPLE 26

Tooth cavity sealers, liners, bases, and pit and fissure sealants containing nano releasing fillers. A cavity sealer containing nano releasing fillers can provide a high level of release at a relatively low filler level due to the extremely high surface area and reactivity of the nano particles. The sealer can be coated to the walls of the prepared tooth cavity and provide a protective coating and a barrier at the interface between the restorative material and the walls.

Cavity liners are cements or resin coating containing nano releasing filler that can achieve a physical barrier and provide a therapeutic effect. They can be applied to dentin cavity walls that are near the pulp.

Cavity bases containing nano releasing fillers can be used to replace missing dentin, for bulk buildup or blocking out undercuts in preparation for indirect restorations.

A pit is a small depression in tooth enamel, usually located in an enamel groove and often at the junction of two or more fissures (Summitt et al., Operative Dentistry, Quintessence, Chicago, 2001). A fissure is a developmental linear cleft usually found at the base of an enamel groove; it is commonly the result of the lack of fusion of the enamel of adjoining dental cusps (Summitt et al., Operative Dentistry, Quintessence, Chicago, 2001). A pit and fissure sealant containing nano releasing fillers can be used to fill these pits and fissures. They can produce a high level of ion release due to the extremely high surface area and reactivity of the nano particles to combat caries. They can also contain strengtheners to provide mechanical integrity and wear resistance on the occlusal surfaces for durability.

The nano particles that can be used in sealers, liners, bases and pit and fissure sealants include DCPD, DCPA, calcium fluoride, tetracalcium phosphate, alpha-tricalcium phosphate, calcium carbonate, beta-tricalcium phosphate, hydroxyapatite (HA), carbonated HA, calcium-deficient HA, poorly crystalline HA, amorphous calcium phosphate-based materials, calcium hydroxide, and combinations thereof. The filler level by mass ranges from 1% to 80%, preferably from 15% to 70%, most preferably from 30% to 60%.

EXAMPLE 27

Figure 11A:
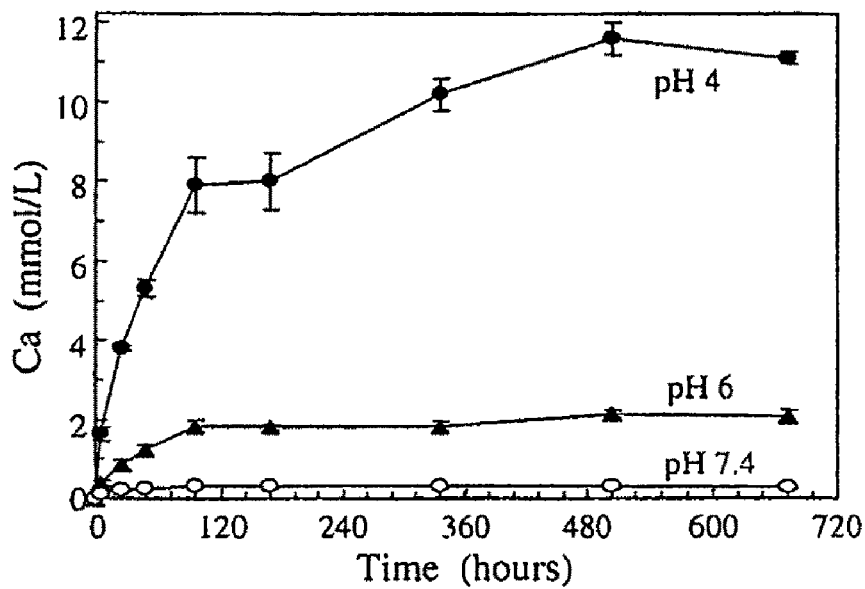
FIGS. 11A and 11B are graphs of Ca and $PO_4$ concentration plotted against time for a DCPA-TTCP composite.
Figure 11B:
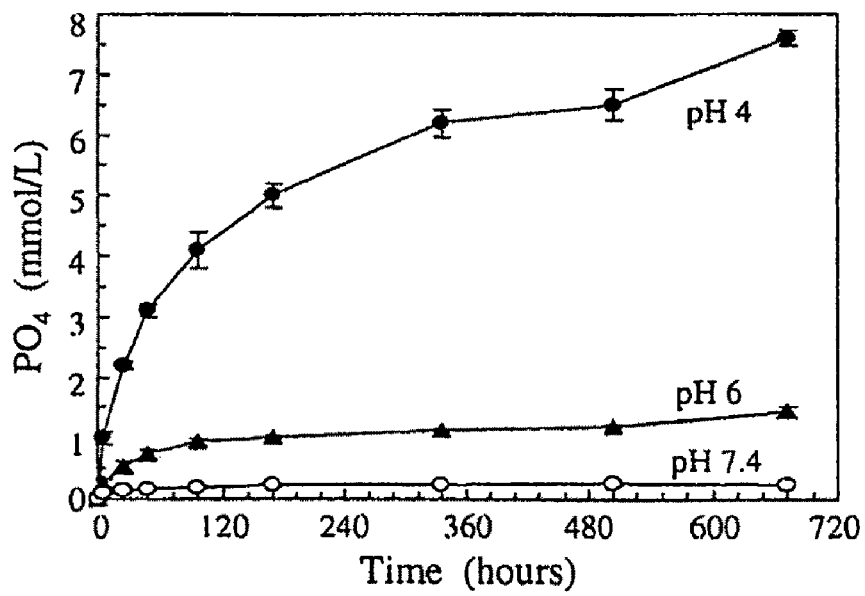

Nano DCPA-TTCP composite that can respond to local changes in oral acidity caused by plaque or cariogenic bacteria. A composite using nano DCPA (112 nm particle size) and TTCP (0.9 µm or 900 nm particle size) particles as fillers in a dental resin can behave in a controlled manner by responding to local changes in oral acidity caused by plaque or cariogenic bacteria. The composite releases little Ca and $PO_4$ at neutral pH, but increases the Ca and $PO_4$ release dramatically when pH is decreased as shown by FIG. 11.

EXAMPLE 28

Figure 12A:
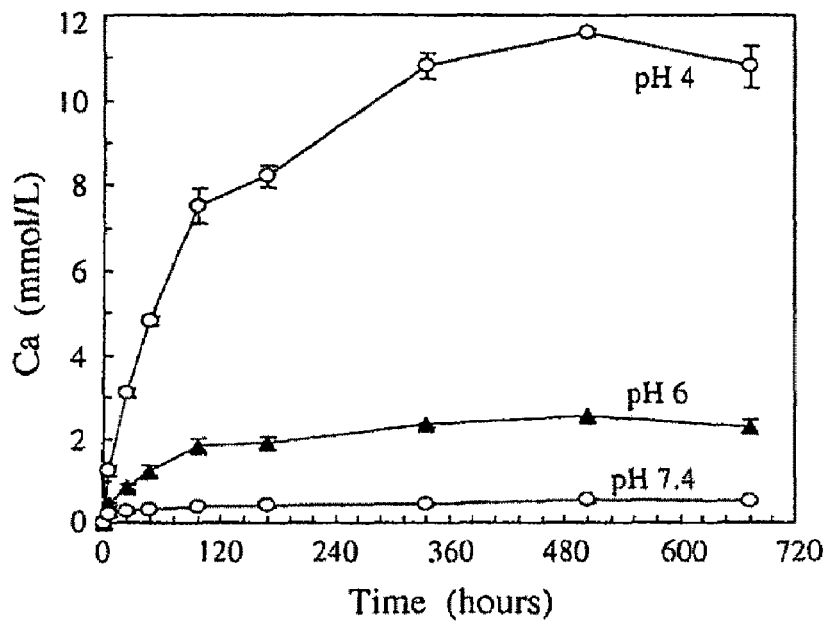
FIGS. 12A and 12B are graphs of Ca and $PO_4$ concentration over time for a TTCP composite.
Figure 12B:
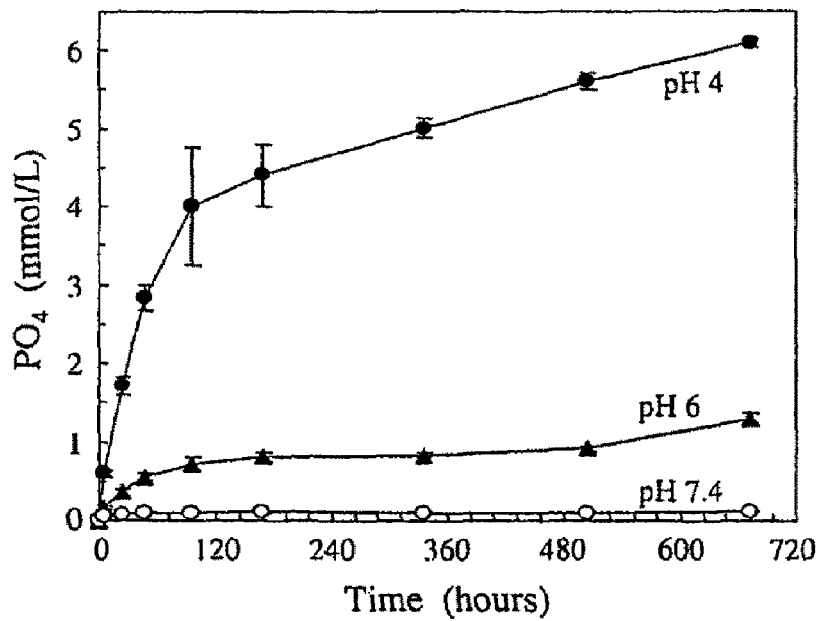

Dental TTCP composite that can respond to local changes in oral acidity caused by plaque or cariogenic bacteria. Another example is a composite using TTCP (0.9 µm or 900 nm particle size) particles as fillers in a dental resin. The composite can behave in a controlled or environmentally reactive manner by responding to local changes in oral acidity caused by plaque or cariogenic bacteria. The composite releases little Ca and $PO_4$ at a neutral pH of 7.4, but increases the Ca and $PO_4$ release dramatically when pH is decreased as illustrated by FIG. 12.

EXAMPLE 29

Figure 13A:
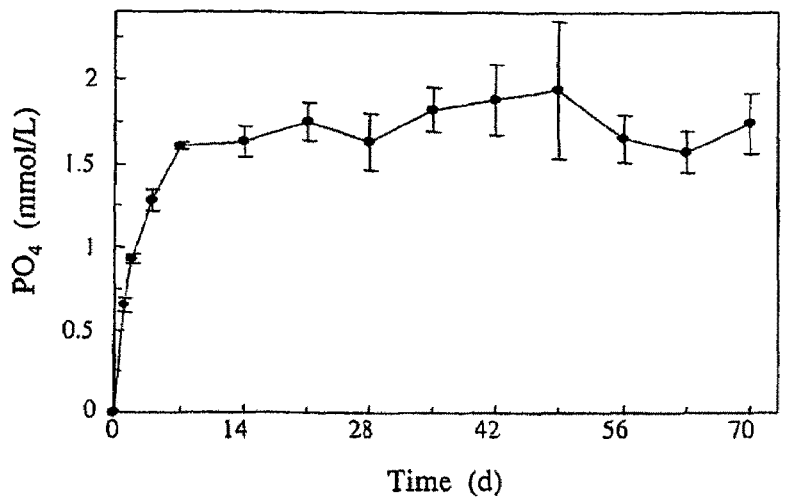
FIGS. 13A, 13B and 13C, respectively, are graphs of $PO_4$ cumulative $F^-$ and $F^-$ release rate over time for a $CaF_2$-DCPA composite.
Figure 13B:
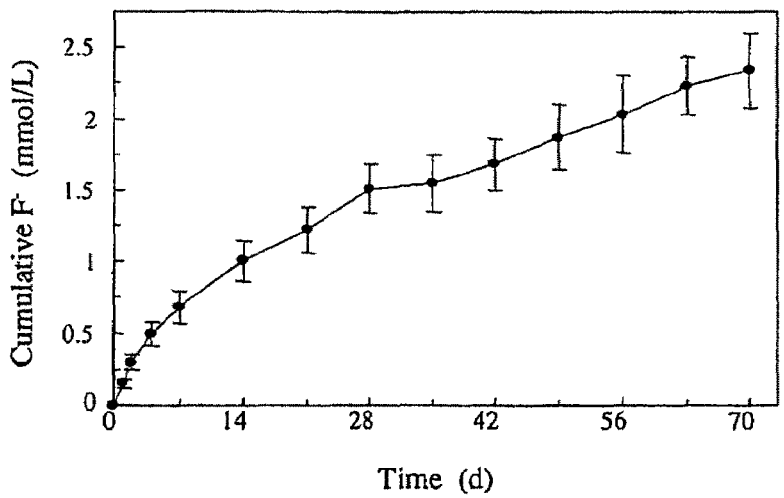
Figure 13C:
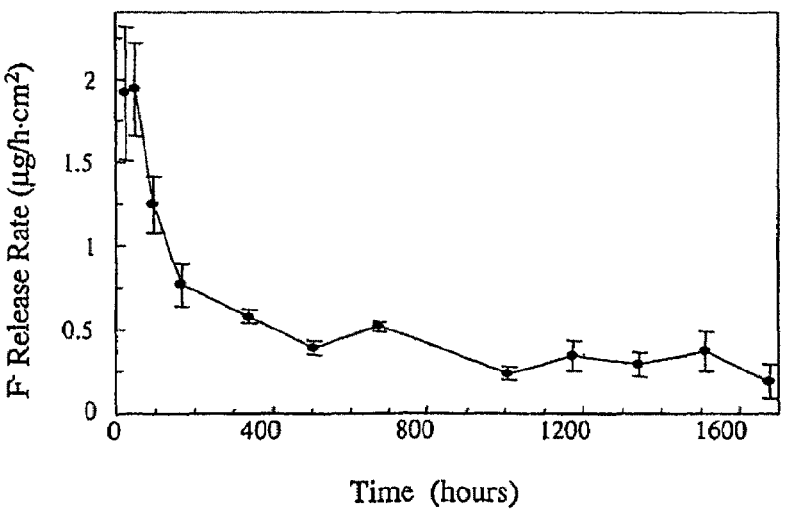
Figure 14A:
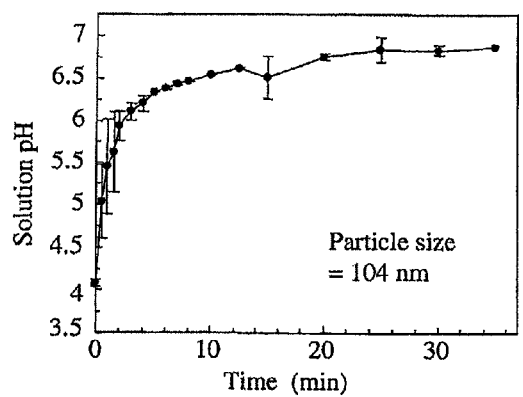
FIGS. 14A, 14B, 14C and 14D are respectively time dependent graphs for a calcium phosphate composite solution pH for various particle sizes as compared to a control.
Figure 14B:
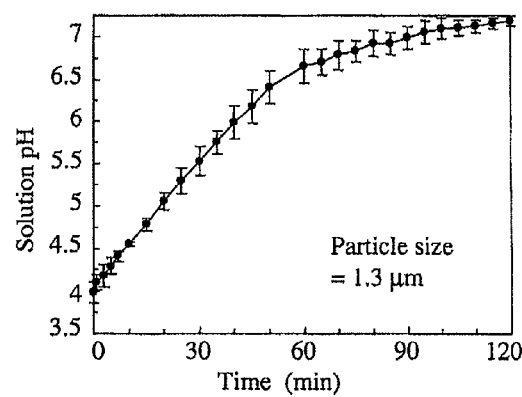
Figure 14C:
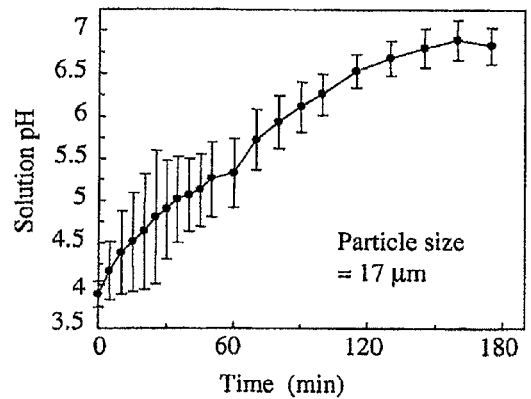
Figure 14D:
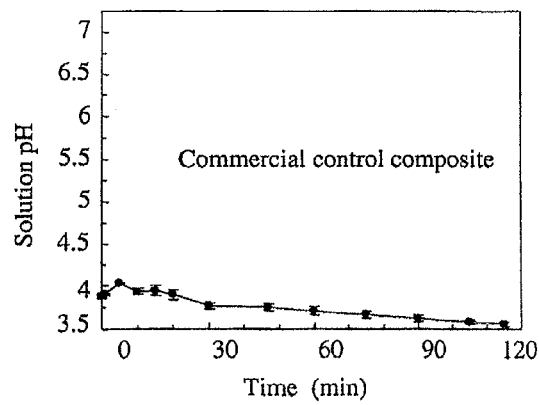

Dental composite that can release calcium or phosphate ions as well as fluoride ions. Another example is a composite using nano DCPA (112 nm particle size) and nano $CaF_2$ (53 nm particle size) particles as fillers in a dental resin. The composite releases cavity fighting components as shown in FIG. 13. The composite flexural strength is measured to be (99.5±7.2) MPa.

EXAMPLE 30

Nano composite that can neutralize the oral acid challenge. Another example is to provide composites using TTCP particles as fillers in a dental resin. The composite can neutralize oral acid caused by plaque or cariogenic bacteria and increase the pH to neutral, thereby inhibiting cavity formation in teeth. The acid neutralization capability is strongly determined by the particle size as demonstrated by FIG. 14. Other composites using ACP and combinations of TTCP-DCPA, TTCP-$CaF_2$, TTCP-ACP, and ACP-$CaF_2$ can also be made.

EXAMPLE 31

Figure 15A:
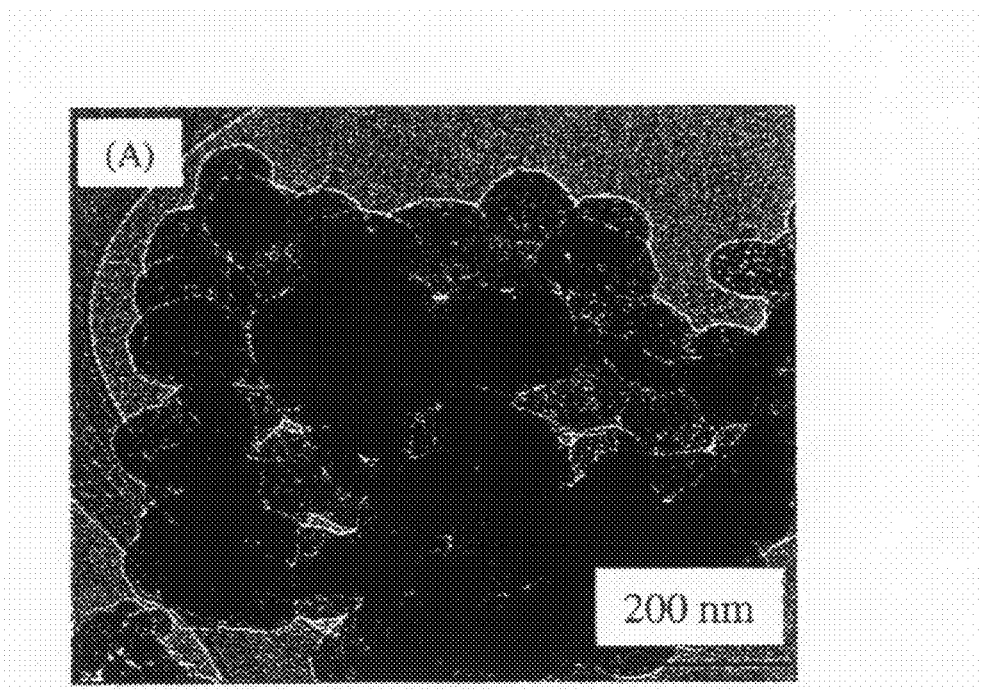
FIGS. 15A and 15B are respectively a TEM and XRD graph for an ACP nanocomposite.
Figure 15B:
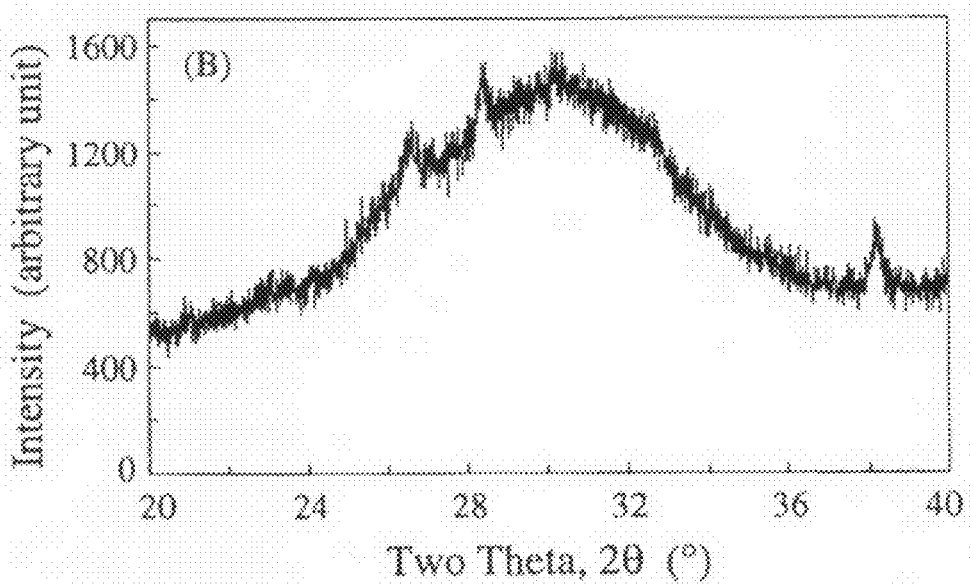

Nano ACPcomposite. Nanoparticles of ACP (amorphous calcium phosphate, $Ca_3[PO_4]_2$) were synthesized using the spray drying method illustrated by FIG. 15. The particle surface area was measured using the BET method to be 17.76 $m^2/g$. With a density of 2.9 $g/cm^3$, the equivalent particle size was estimated to be 116 nm. Nano ACP dental composite specimens were made by using a two-part-chemically-cured Bis-GMA-TEGDMA resin filled with 70% by mass of nano ACP and silica-fused silicon nitride whiskers at nano ACP: whisker mass ratio of 1:2. The flexural strength of these specimens (mean±sd; n=5) was measured to be (132±19) MPa, matching the (112±22) MPa of a commercial stress-bearing composite without Ca—$PO_4$ (TPH, Caulk/Dentsply, Milford, Del.) (p>0.1).

SUMMARY

Combining nanosized particles which comprise a source of desired dental restorative, repair or therapeutic materials with strengthening agents in various forms such as whiskers, fibers, particles and the like in a resin matrix results in a highly strain resistant, high strength composite which more effectively releases the therapeutic agents. Importantly, the utilization of nanosized particles of the restorative or therapeutic material in the combination enables observation of significantly improved results in the context of therapeutic delivery of the materials. Thus combining delivery of therapeutic materials with strengtheners as fillers in an appropriate matrix, provides a significantly useful product for dental and/or bone repair.

Variations of the combinations of component parts may be used without departing from the spirit and scope of the invention which is limited only by the following claims and equivalents thereof.

What is claimed is:

1. A dental restorative composite consisting essentially of:
   (a) a filler of nano particles of dicalcium phosphate anhydrous (DCPA) having a particle size in the range of about 50 nm to 200 nm;
   (b) a strengthener of SiC generally in the ratio of about 1:1 with respect to DCPA, said strengthener in the form of particles, said filler nano particles and strengthener comprising at least 60% of the mass fraction of the composite; and
   (c) a chemically curable resin including bisphenol glycidyl methacrylate (Bis-GMA), said composite in the form of a hardenable paste.

2. The composite of claim 1 further including $Si_3N_4$ as additional strengthener in substitution for at least a portion of said SiC.

3. The composite of claim 1 wherein said strengthener is in the form of nano particles in the range of 40 nm to 80 nm.

4. The composite of claim 1 further including $CaF_2$ nano particles as an additional filler constituent.

5. A dental restorative composite consisting essentially of:
   (a) a filler of nano particles of dicalcium phosphate anhydrous (DCPA) having a particle size in the range of about 50 nm to 200 nm;
   (b) a strengthener of SiC generally in the ratio of about 1:1 with respect to DCPA, said strengthener in the form of particles, said filler nano particles and strengthener comprising at least 60% of the mass fraction of the composite;
   (c) a chemically curable resin including bisphenol glycidyl methacrylate (Bis-GMA), said composite in the form of a hardenable paste; and
   (d) further including as an additional filler nano particles of $CaF_2$ having a particle size in the range of about 50 nm to 200 nm.

* * * * *